United States Patent
Raslambekov

(10) Patent No.: US 11,278,377 B1
(45) Date of Patent: Mar. 22, 2022

(54) SYSTEM AND METHOD FOR PERFORMING DIGITAL SEPARATION OF TEETH

(71) Applicant: Oxilio Ltd, Larnaca (CY)

(72) Inventor: Islam Khasanovich Raslambekov, Long Island City, NY (US)

(73) Assignee: Oxilio Ltd, Larnaca (CY)

( * ) Notice: Subject to any disclaimer, the term of this patent is extended or adjusted under 35 U.S.C. 154(b) by 0 days.

(21) Appl. No.: 17/337,363

(22) Filed: Jun. 2, 2021

(51) Int. Cl.
*G06T 17/20* (2006.01)
*A61C 7/00* (2006.01)

(52) U.S. Cl.
CPC .............. *A61C 7/002* (2013.01); *G06T 17/20* (2013.01); *G06T 2210/12* (2013.01); *G06T 2210/41* (2013.01); *G06T 2219/008* (2013.01); *G06T 2219/2004* (2013.01)

(58) Field of Classification Search
CPC combination set(s) only.
See application file for complete search history.

(56) References Cited

U.S. PATENT DOCUMENTS

| | | |
|---|---|---|
| 6,371,761 B1 | 4/2002 | Cheang et al. |
| 6,409,504 B1 | 6/2002 | Jones et al. |
| 6,688,886 B2 | 2/2004 | Hughes et al. |
| 7,110,594 B2 | 9/2006 | Jones et al. |
| 7,689,398 B2 | 3/2010 | Cheng et al. |
| 9,129,363 B2 | 9/2015 | Chen et al. |
| 10,535,203 B2 | 1/2020 | Huang et al. |
| 10,617,489 B2 | 4/2020 | Grove et al. |
| 10,722,328 B2 | 7/2020 | Velazquez et al. |

| | | | |
|---|---|---|---|
| 2002/0015934 A1* | 2/2002 | Rubbert | G06T 17/00 433/29 |
| 2003/0214501 A1* | 11/2003 | Hultgren | G06T 19/20 345/419 |
| 2008/0248443 A1* | 10/2008 | Chishti | A61C 7/08 433/24 |
| 2009/0098502 A1* | 4/2009 | Andreiko | G16H 50/50 433/24 |
| 2010/0085273 A1* | 4/2010 | Nakayama | G06T 19/003 345/1.1 |

(Continued)

FOREIGN PATENT DOCUMENTS

| | | |
|---|---|---|
| EP | 3673864 A1 | 7/2020 |
| WO | WO-2021145544 A1 * | 7/2021 ............... A61C 9/00 |

OTHER PUBLICATIONS

US 10,617,489, 08/2004, Wagner et al. (withdrawn)

*Primary Examiner* — Andrew G Yang
(74) *Attorney, Agent, or Firm* — BCF LLP

(57) ABSTRACT

The disclosed systems and methods are for performing digital separation of teeth. The method includes: (i) obtaining a 3D digital model of two adjacent teeth, wherein the 3D digital model includes a first set of elements comprising first tooth elements and second tooth elements, (ii) generating a separation plane relative to the two adjacent teeth by: obtaining a second set of elements associated with a separation zone, identifying a third set of elements which are a subset of the second set of elements, and determining the separation plane, (iv) performing the digital separation by generating a first cutting plane and a second cutting plane, and (v) updating the 3D digital model by removing the first tooth elements and the second tooth elements which are between the first and second cutting planes, and (vi) storing the updated 3D digital model in a memory.

18 Claims, 19 Drawing Sheets

(56) References Cited

U.S. PATENT DOCUMENTS

| | | | |
|---|---|---|---|
| 2018/0250744 A1* | 9/2018 | Symeonidis | B23K 26/034 |
| 2018/0268545 A1* | 9/2018 | Feng | G16H 50/50 |
| 2019/0197691 A1 | 11/2019 | Shi et al. | |
| 2019/0357997 A1 | 11/2019 | Shi et al. | |

* cited by examiner

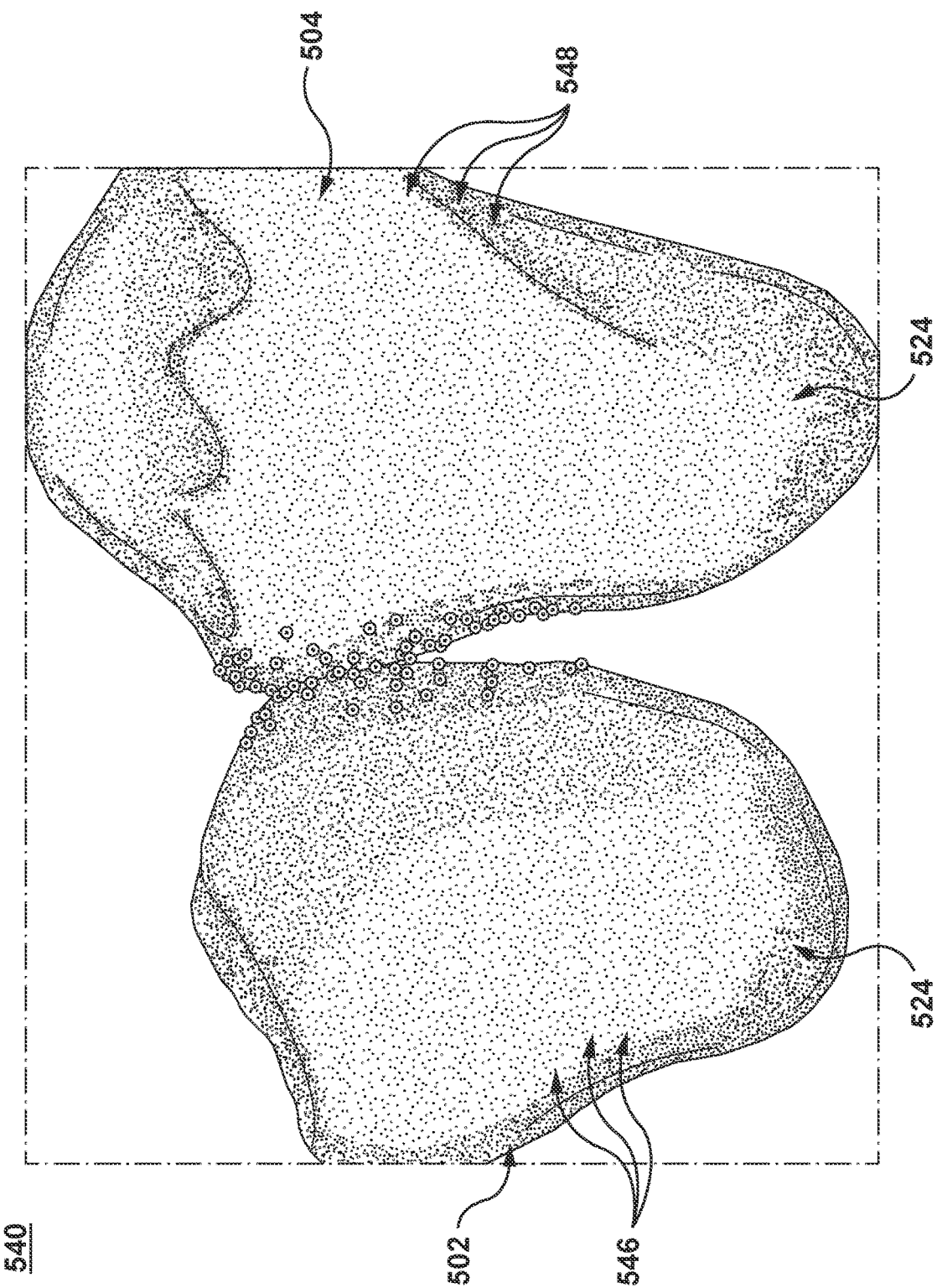

SYSTEM AND METHOD FOR PERFORMING DIGITAL SEPARATION OF TEETH

TECHNICAL FIELD

The present technology relates, generally, to orthodontic treatment planning, and in particular to a system and method for performing digital separation of teeth.

BACKGROUND

In the field of orthodontic treatment, an orthodontic practitioner may need to physically remove enamel from tooth surface(s) of adjacent teeth as part of an orthodontic treatment, such as to avoid collisions between the teeth during orthodontic treatment, correct crowding, or reshape the contact area between the adjacent teeth. This is known as Interproximal Reduction (IPR). The IPR may be needed in one or more steps of the orthodontic treatment.

Teeth which have had enamel removed therefrom through IPR will have altered external surfaces. Digitally modelling the altered external surfaces of the teeth may be useful in planning subsequent steps of the orthodontic treatment, or for providing assistance to the orthodontic practitioner in executing the IPR.

Therefore, there is a need to model such a process and more specifically to recreate tooth geometries of the adjacent teeth in a tooth model after the IPR. Thus, there is an interest in developing an efficient process of determining and performing digital teeth separation.

Certain prior art approaches have been proposed to address the technical problem of removing enamel from tooth surface(s).

U.S. Pat. No. 7,689,398-B2 issued on Mar. 30, 2010, assigned to Align Technology, Inc, and entitled "System and method for modeling and application of interproximal reduction of teeth" discloses system and method for modeling and application of interproximal reduction (IPR) of teeth to facilitate orthodontic treatment. In accordance with an exemplary embodiment, a system and method for modeling and application of IPR are configured within a treatment methodology that initially determines whether stripping is needed for two neighboring teeth. If stripping is necessary, the exemplary method for modeling and application of IPR is conducted. In an exemplary embodiment, a stripping plane or other surface is constructed to determine the amount and region of stripping for two neighboring teeth, in other words, the volume to be removed between two neighboring teeth. After stripping of the tooth, the tooth geometry can be reconstructed to enable application of the IPR tooth model, such as enabling the clinician to utilize the IPR tooth model for teeth movement planning.

U.S. Pat. No. 6,371,761-B1 issued on Apr. 16, 2002, assigned to Align Technology, Inc, and entitled "Flexible plane for separating teeth models" discloses a computer-implemented method that separates first and second portions of a tooth by defining a cutting surface intersecting the first and second portions; and applying the cutting surface to the tooth to separate the tooth into two portions.

U.S. Pat. No. 6,409,504-B1 issued on Jun. 25, 2002, assigned to Align Technology, Inc, and entitled "Manipulating a digital dentition model to form models of individual dentition component" discloses a programmed computer used to create a digital model of an individual component of a patient's dentition. The computer obtains a 3D digital model of the patient's dentition, identifies points in the dentition model that lie on an interproximal margin between adjacent teeth in the patient's dentition, and uses the identified points to create a cutting surface that separates portions of the dentition model representing the adjacent teeth.

SUMMARY

The embodiments of the present disclosure have been developed based on developers' appreciation of shortcomings associated with the prior art.

Various embodiments of the present technology have been developed based on the developers' appreciation of an efficient method for performing digital separation between a 3D digital model of two adjacent teeth and appreciation of how such digital separation may be used in the course of an orthodontic treatment planning.

Broadly, methods and systems for performing such a digital separation between a 3D digital model of two adjacent teeth comprise identifying elements in the 3D digital model to be used in determining a separation plane between the two adjacent teeth; determining the separation plane including a position in space of the separation plane; and updating the 3D digital model of the two adjacent teeth based on the determined separation plane to model removal of material from one or both of the two adjacent teeth.

More specifically, in various non-limiting embodiments, based on the separation plane, a first cutting plane and a second cutting plane is generated. The 3D digital model of the two adjacent teeth can be updated by removing elements of the 3D digital model between the first cutting plane and the second cutting plane.

Systems and/or methods for performing digital separation may be beneficial when planning an orthodontic treatment for the patient, using for example automated or semi-automated orthodontic treatment planners. Also, systems and/or methods for performing digital separation may provide an extra degree of freedom to the orthodontic practitioner to physically remove enamel from tooth surface(s) of adjacent teeth in order to physically separate the adjacent teeth. As such, the orthodontic practitioner may utilize the 3D digital model to analyze the amount of separation between the two adjacent teeth and if required, the orthodontic practitioner may alter the 3D digital model by changing various parameters, such as in an interactive user interface.

In certain embodiments, modelling the digital separation including the altered external surfaces of the two adjacent teeth may assist in accurately determining required movements of the teeth to desired positions whilst avoiding collisions and changes to the bite.

In certain embodiments, modelling the digital separation including the altered external surfaces of the two adjacent may assist in determining correct placement of orthodontic appliances relative to the altered external surfaces of the teeth after the physical IPR.

In certain embodiments, modelling the digital separation including the altered external surfaces of the two adjacent may also be useful in validating the given IPR process as part of the orthodontic treatment plan, or for assisting the orthodontic practitioner plan and execute the IPR, such as by locating the correct region on the adjacent teeth from which to remove the enamel.

In addition to the benefits to the orthodontic practitioner, the systems and/or methods for performing digital separation may improve a computation efficiency of the computational resources. By way of an example, in order to generate the separation plane, systems and/or methods may rely on various computationally efficient techniques and thereby improving the performance of the computational resources. More specifically, in certain embodiments, reducing a number of vertices for analysis can speed up generation of the separation plane.

In accordance with a first broad aspect of the present disclosure, there is provided a method for performing digital separation of two adjacent teeth of a plurality of teeth of a patient, the method executable by a processor of a computer system, the method comprising: obtaining a 3D digital model of the two adjacent teeth, the two adjacent teeth comprising a first tooth and a second tooth, wherein the 3D digital model includes a first set of elements comprising first tooth elements representing a first outer geometry of the first tooth and second tooth elements representing a second outer geometry of the second tooth; generating a separation plane relative to the first tooth and the second tooth by: obtaining a second set of elements associated with a separation zone of the two adjacent teeth, the second set of elements comprising a first subset of the first set of elements; identifying a third set of elements which are a second subset of the second set of elements, such that the third set of elements includes a first portion of the first tooth elements in the separation zone being within a threshold distance from a second portion of the second tooth elements in the separation zone, and determining the separation plane based on the identified third set of elements; performing the digital separation by generating a first cutting plane and a second cutting plane, the first cutting plane being parallel to the separation plane and spaced therefrom towards the first tooth by a first separation distance, and the second cutting plane being parallel to the separation plane and spaced therefrom towards the second tooth by a second separation distance; updating the 3D digital model by removing the first tooth elements and the second tooth elements which are between the first cutting plane and the second cutting plane, the updated 3D digital model representing the digitally separated two adjacent teeth; and storing the updated 3D digital model in a memory of the computer system.

In some embodiments of the method, the threshold distance is a predetermined distance, and if the first outer geometry of the first tooth and the second outer geometry of the second tooth overlap with each other, the identifying the third set of elements comprises identifying element pairs, each element pair comprising a first element associated with the first tooth elements and a second element associated with the second tooth elements that are within the predetermined distance.

In some embodiments of the method, the threshold distance is a summation of a shortest distance between any two elements of the first tooth elements and the second tooth elements and a predetermined distance, and if the first outer geometry of the first tooth and the second outer geometry of the second tooth do not overlap with each other, the identifying the third set of elements comprises: identifying a closest element pair comprising a first element associated with the first tooth elements and a second element associated with the second tooth elements that are separated by the shortest distance, and determining the third set of elements comprises identifying element pairs, each element pair comprising the first element associated with the first tooth elements and the second element associated with the second tooth elements that are within the summation of the shortest distance and the predetermined distance.

In some embodiments of the method, the method further comprising computing the shortest distance by one or more of: using a bounding volume hierarchy (BVH) structure; converting at least one of the first outer geometry and the second outer geometry into a distance field data structure; reducing a dimensionality of the first set of elements in the 3D digital model of the two adjacent teeth from 3D Cartesian coordinates to 2D UV Cartesian coordinates.

In some embodiments of the method, the distance field data structure includes precomputed shortest distances from the first tooth elements to the second tooth elements.

In some embodiments of the method, the reducing the dimensionality of the first set of elements in the 3D digital model of the two adjacent teeth includes: defining a uniform 2D grid representing the 3D digital model, the 2D grid including a plurality of 2D grid cells such that a given 2D grid cell of the plurality of 2D grid cells corresponds to a respective one of the first tooth elements and the second tooth elements of the first set of elements in the 3D digital model; and assigning, to each one of the plurality of 2D grid cells, a first depth value and a second depth value, the second depth value being greater than the first depth value.

In some embodiments of the method, the method further comprises computing the shortest distance between the first element associated with the first tooth elements and the second element associated with the second tooth elements based on the first depth value, the second depth value.

In some embodiments of the method, the determining the separation plane according to the identified third set of elements includes a planar fitting of coordinates of the identified third set of elements based on linear regression and the threshold distance.

In some embodiments of the method, the first separation distance is equal to the second separation distance.

In some embodiments of the method, the first separation distance is different from the second separation distance.

In some embodiments of the method, the 3D digital model is based on at least one of: axis-aligned bounding boxes (AABB) and the first set of elements representing the first outer geometry and the second outer geometry comprise a set of AABA vertices; a 3D point cloud and the first set of elements representing the first outer geometry and the second outer geometry comprise points; a polygon mesh and the first set of elements representing the first outer geometry and the second outer geometry comprise a set of mesh vertices.

In some embodiments of the method, the method further comprising, generating an orthodontic treatment plan for the patient in accordance with the updated 3D digital model.

In some embodiments of the method, the method further comprising, displaying the orthodontic treatment plan.

In some embodiments of the method, the method further comprising, displaying the updated 3D digital model.

In some embodiments of the method, at least some of the first tooth elements and the second tooth elements of the second set of elements associated with the first tooth are projected on the first cutting plane, at least some of the first tooth elements and the second tooth elements of the second set of elements associated with the second tooth are projected on the second cutting plane, and the updating the 3D digital model, further comprises, removing the elements of the second set of elements projected on the first cutting plane and the second cutting plane.

In some embodiments of the method, the separation zone includes an interdental region between the first tooth and the second tooth In accordance with a second broad aspect of the present disclosure, there is provided a system for performing digital separation of two adjacent teeth of a plurality of teeth of a patient, the system comprising a computer system having a processor, the processor configured to execute a method comprising: obtaining a 3D digital model of the two adjacent teeth, the two adjacent teeth comprising a first tooth and a second tooth, wherein the 3D digital model includes a first set of elements comprising first tooth elements representing a first outer geometry of the first tooth and second tooth elements representing a second outer geometry of a the second tooth; generating a separation plane relative to the first tooth and the second tooth by: obtaining a second set of elements associated with a separation zone of the two adjacent teeth, the second set of elements comprising a first subset of the first set of elements; identifying a third set of elements which are a second subset of the second set of elements, such that the third set of elements includes a first portion of the first tooth elements in the separation zone being within a threshold distance from a second portion of the second tooth elements in the separation zone, and determining the separation plane based on the identified third set of elements; performing the digital separation by generating a first cutting plane and a second cutting plane, the first cutting plane being parallel to the separation plane and spaced therefrom towards the first tooth by a first separation distance, and the second cutting plane being parallel to the separation plane and spaced therefrom towards the second tooth by a second separation distance; updating the 3D digital model by removing the first tooth elements and the second tooth elements which are between the first cutting plane and second cutting plane, the updated 3D digital model representing the digitally separated two adjacent teeth; and storing the updated 3D digital model in a memory of the computer system.

In some embodiments of the system, the threshold distance is a predetermined distance, and if the first outer geometry of the first tooth and the second outer geometry of the second tooth overlap with each other, the identifying the third set of elements comprises identifying element pairs, each element pair comprising a first element associated with the first tooth elements and a second element associated with the second tooth elements that are within the predetermined distance.

In some embodiments of the system, the threshold distance is a summation of a shortest distance between any two elements of the first tooth elements and the second tooth elements and a predetermined distance, and if the first outer geometry of the first tooth and the second outer geometry of the second tooth do not overlap with each other, the identifying the third set of elements comprises: identifying a closest element pair comprising a first element associated with the first tooth elements and a second element associated with the second tooth elements that are separated by the shortest distance, and determining the third set of elements comprises identifying element pairs, each element pair comprising the first element associated with the first tooth elements and the second element associated with the second tooth elements that are within the summation of the shortest distance and the predetermined distance.

In some embodiments of the system, the determining the separation plane according to the identified third set of elements includes a planar fitting of coordinates of the identified third set of elements based on linear regression and the threshold distance.

BRIEF DESCRIPTION OF THE FIGURES

Further features and advantages of the present disclosure will become apparent from the following detailed description, taken in combination with the appended drawings, in which:

FIG. 5 illustrates another 3D digital model representing the first tooth and the second tooth being represented as 3D point cloud, in accordance with various non-limiting embodiments of the present technology;

Figure 1:
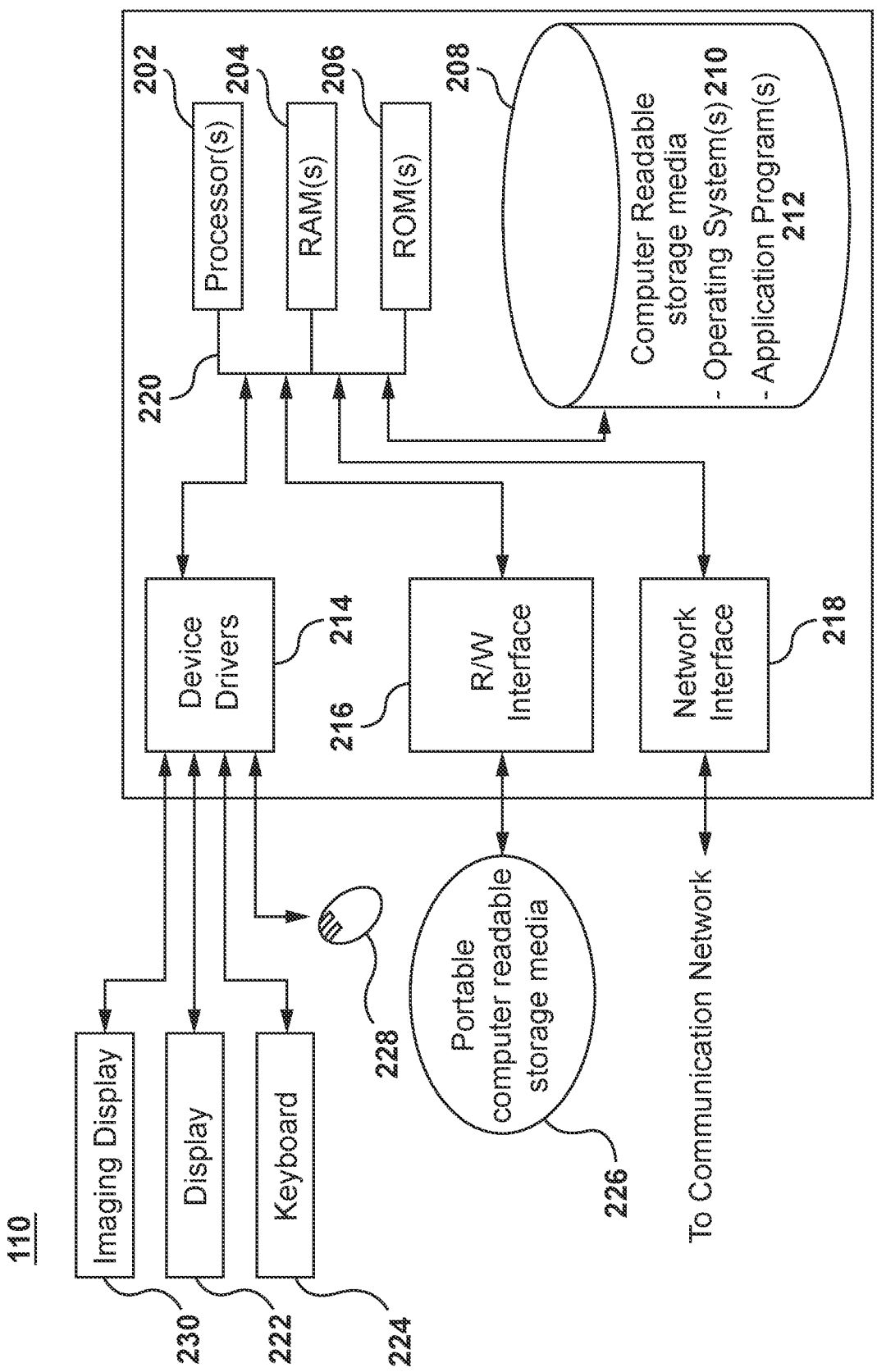
FIG. 1 depicts a high-level block diagram of components of a computer system, in accordance with various non-limiting embodiments of the present disclosure.

It is to be understood that throughout the appended drawings and corresponding descriptions, like features are identified by like reference characters. Furthermore, it is also to be understood that the drawings and ensuing descriptions are intended for illustrative purposes only and that such disclosures do not provide a limitation on the scope of the claims.

DETAILED DESCRIPTION

The instant disclosure is directed to address at least some of the deficiencies of the prior art. In particular, the instant disclosure describes a system and method for performing digital separation of teeth.

Unless otherwise defined or indicated by context, all technical and scientific terms used herein have the same meaning as commonly understood by one of ordinary skill in the art to which the described embodiments appertain to.

In the context of the present specification, "computer system" is any computer hardware that is capable of running software appropriate to the relevant task at hand. In the context of the present specification, in general the term "computer system" is associated with a user of the computer system. Thus, some (non-limiting) examples of computer systems include personal computers (desktops, laptops, netbooks, etc.), smartphones, and tablets, as well as network equipment such as routers, switches, and gateways. It should be noted that a device acting as a computer system in the present context is not precluded from acting as a server to other computer systems. The use of the expression "a computer system" does not preclude multiple computer systems being used in receiving/sending, carrying out or causing to be carried out any task or request, or the consequences of any task or request, or steps of any method described herein.

In the context of the present specification, unless provided expressly otherwise, the words "first", "second", "third", etc. have been used as adjectives only for the purpose of allowing for distinction between the nouns that they modify from one another, and not for the purpose of describing any particular relationship between those nouns. Thus, for example, it should be understood that, the use of the terms "first processor" and "third processor" is not intended to imply any particular order, type, chronology, hierarchy or ranking (for example) of/between the server, nor is their use (by itself) intended to imply that any "second server" must necessarily exist in any given situation. Further, as is discussed herein in other contexts, reference to a "first" element and a "second" element does not preclude the two elements from being the same actual real-world element. Thus, for example, in some instances, a "first" server and a "second" server may be the same software and/or hardware, in other cases they may be different software and/or hardware.

It will be understood that when an element is referred to as being "connected" or "coupled" to another element, it can be directly or indirectly connected or coupled to the other element or intervening elements that may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

In the context of the present specification, when an element is referred to as being "associated with" another element, in certain embodiments, the two elements can be directly or indirectly linked, related, connected, coupled, the second element employs the first element, or the like without limiting the scope of the present technology.

The terminology used herein is only intended to describe particular representative embodiments and is not intended to be limiting of the present technology. As used herein, the singular forms "a," "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

Implementations of the present technology each have at least one of the above-mentioned objects and/or aspects, but do not necessarily have all of them. It should be understood that some aspects of the present technology that have resulted from attempting to attain the above-mentioned object may not satisfy this object and/or may satisfy other objects not specifically recited herein.

The examples and conditional language recited herein are principally intended to aid the reader in understanding the principles of the present technology and not to limit its scope to such specifically recited examples and conditions. It will be appreciated that those skilled in the art may devise various arrangements which, although not explicitly described or shown herein, nonetheless embody the principles of the present technology and are included within its spirit and scope.

Furthermore, as an aid to understanding, the following description may describe relatively simplified implementations of the present technology. As persons skilled in the art would understand, various implementations of the present technology may be of a greater complexity.

In some cases, what are believed to be helpful examples of modifications to the present technology may also be set forth. This is done merely as an aid to understanding, and, again, not to define the scope or set forth the bounds of the present technology. These modifications are not an exhaustive list, and a person skilled in the art may make other modifications while nonetheless remaining within the scope of the present technology. Further, where no examples of modifications have been set forth, it should not be interpreted that no modifications are possible and/or that what is described is the sole manner of implementing that element of the present technology.

Moreover, all statements herein reciting principles, aspects, and implementations of the present technology, as well as specific examples thereof, are intended to encompass both structural and functional equivalents thereof, whether they are currently known or developed in the future. Thus, for example, it will be appreciated by those skilled in the art that any block diagrams herein represent conceptual views of illustrative circuitry embodying the principles of the present technology. Similarly, it will be appreciated that any flowcharts, flow diagrams, state transition diagrams, pseudocode, and the like represent various processes which may be substantially represented in computer-readable media and so executed by a computer or processor, whether or not such computer or processor is explicitly shown.

The functions of the various elements shown in the figures, including any functional block labeled as a "processor" or a "processing unit", may be provided through the use of dedicated hardware as well as hardware capable of executing software in association with appropriate software. When provided by a processor, the functions may be provided by a single dedicated processor, by a single shared processor, or by a plurality of individual processors, some of which may be shared. In some embodiments of the present technology, the processor may be a general-purpose processor, such as a central processing unit (CPU) or a processor dedicated to a specific purpose, such as a graphics processing unit (GPU), or a neural processing unit (NPU). Moreover, explicit use of the term "processor" or "controller" should not be construed to refer exclusively to hardware capable of executing software, and may implicitly include, without limitation, digital signal processor (DSP) hardware, network processor, application specific integrated circuit (ASIC), field programmable gate array (FPGA), read-only memory (ROM) for storing software, random access memory (RAM), and non-volatile storage. Other hardware, conventional and/or custom, may also be included.

In the context of the present disclosure, unless expressly indicated otherwise, a "database" is any structured collection of data, irrespective of its particular structure, the database management software, or the computer hardware on which the data is stored, implemented or otherwise rendered available for use. A database may reside on the same hardware as the process that stores or makes use of the information stored in the database or it may reside on separate hardware, such as a dedicated server or plurality of servers.

Software modules, modules, or units which are implied to be software, may be represented herein as any combination of flowchart elements or other elements indicating performance of process steps and/or textual description. Such modules may be executed by hardware that is expressly or implicitly shown.

With these fundamentals in place, the instant disclosure is directed to address at least some of the deficiencies of the current technology. In particular, the instant disclosure describes a system and method for performing digital separation of teeth.

FIG. 1 depicts a high-level block diagram of components of a computer system 110, in accordance with various non-limiting embodiments of the present disclosure. It should be appreciated that FIG. 1 provides only an illustration of one implementation of the computer system 110 and does not imply any limitations with regard to the environments in which different embodiments may be implemented. Various modifications to the depicted environment may be done to implement the computer system 110 without departing from the principles presented herein. The computer system 110 may be a server, a desktop computer, a laptop computer, or any device that may be configured to implement the present technology, as should be understood by a person skilled in the art.

As shown, the computer system 110 employs one or more different type of processors 202, one or more computer-readable random access memories (RAMs) 204, one or more computer-readable read only memories (ROMs) 206, one or more computer-readable storage media 208, device drivers 214, a read/write (R/W) driver interface 216, a network interface 218, all interconnected over a communication fabric 220. The communication fabric 220 may be implemented by any architecture designed for communicating data and/or control information between processors (such as microprocessors, communications and network processors, etc.), system memory, peripheral devices, and any other hardware components within a system.

The processor 202 of the computer system 110 may include one or more of a CPU, an accelerator, a microprocessor, GPU, an NPU, an ASIC, a FPGA, a dedicated logic circuitry, a dedicated artificial intelligence processor unit, or combinations thereof.

One or more operating systems 210 and one or more application programs 212 (examples of application programs may include programming instructions) are stored on one or more of computer-readable storage media 208 for execution by one or more of the processors 202 via one or more of respective RAMs 204 (which typically include a cache memory). In the illustrated embodiment, each of the computer-readable storage media 208 may be embodied as a magnetic disc storage device of an internal hard drive, compact disc read-only memory (CD-ROM), digital video disc (DVD), memory stick, magnetic tape, magnetic disk, optical disk, a semiconductor storage device such as RAM, ROM, erasable programmable read-only memory (EPROM), flash memory or any other computer-readable tangible storage device that can store a computer program and digital information. The one or more RAMs 204, one or more ROMs 206 and/or the computer-readable storage media 208 may be configured in any known manner and arranged to store, among other data, one or more of: set-up data, patient data, patient medical records of one or more patients, 3D digital model of teeth including, and/or orthodontic treatment data.

The R/W driver interface 216 reads from and writes to one or more portable computer-readable storage media 226. The application programs 212 may be related to the malicious data assessment among various web-resources and stored on one or more of portable computer-readable storage media 226, read via the respective R/W driver interface 216 and loaded into the respective computer-readable storage media 208.

Further, the network interface 218 may be based on a transmission control protocol/internet protocol (TCP/IP) adapter card or wireless communication adapter (such as a wireless communication adapter using orthogonal frequency division multiple access (OFDMA) technology). The application programs 212 on the computer system 110 may be downloaded to the computer system 110 from an external computer or external storage device via a communication network (for example, the Internet, a local area network or other wide area network or wireless network) and the network interface 218. From the network interface 218, the application programs 212 may be loaded onto the computer-readable storage media 208. The computer system 110 may connect to routers, firewalls, switches, gateway computers and/or edge servers of the communication network using copper wires, optical fibers, wireless transmission, and the like.

The computer system 110 may also include a display screen 222, a keyboard or keypad 224, a computer mouse or touchpad 228 and an imaging device 230. The device drivers 214 may interface with the display screen 222 for imaging, with the keyboard or the keypad 224, with the computer mouse or touchpad 228, with the display screen 222 (which may be a touch sensitive display) for alphanumeric character entry and user selections and with the imaging device 230 for scanning or capturing images of the teeth of a patient. The device drivers 214, the R/W driver interface 216 and the network interface 218 may comprise hardware and software (stored on the computer-readable storage media 208 and/or the ROM 206).

In certain non-limiting embodiments, the imaging device 230 may be implemented as any imaging system that is configured to capture and/or process images of a patient's oral region. In some embodiments, it is contemplated that the imaging device 230 may be configured to capture and/or process images of teeth and/or surrounding tissues of the patient's mouth. For instance, the information representative of at least a portion of the oral region of the patient may be composed, at least partially, of the images captured and/or processed by the imaging device 230.

In some embodiments, the images captured and/or processed by the imaging device 230 may include, but are not limited to: images of crown portions of teeth (internal and/or external), images of root portions of teeth (internal and/or external), images of tissues surrounding the teeth, images of nerve pathways in the teeth and/or in the surrounding tissues, images of bones such as jaw bones, other images of the oral region, and the like.

In certain embodiments, the image data received from the imaging device 230 is indicative of properties of anatomical structures of the patient, including: teeth, intraoral mucosa, maxilla, mandible, temporomandibular joint, and nerve pathways, among other structures. In some embodiments, at least some of the image data is indicative of properties of external portions of the anatomical structures, for example dimensions of a gingival sulcus, and dimensions of an external portion of a tooth (e.g., a crown of the tooth) extending outwardly of the gingival sulcus. In some embodiments, the image data is indicative of properties of internal portions of the anatomical structures, for example volumetric properties of bone surrounding an internal portion of the tooth (e.g., a root of the tooth) extending inwardly of the gingival sulcus. Under certain circumstances, such volumetric properties may be indicative of periodontal anomalies which may be factored into an orthodontic treatment plan. In some embodiments, the image data includes cephalometric image datasets. In some embodiments, the image data includes datasets generally intended for the practice of endodontics. In some embodiments, the image data includes datasets generally intended for the practice of periodontics.

It should be noted that images captured and/or processed by the imaging device 230 may be in 2D and/or 3D. Further, in certain non-limiting embodiments of the present technology, the image data includes 2D data, from which 3D data may be derived, and vice versa. For example, the images captured and/or processed by the imaging device 230 may be, but are not limited to: computed tomography (CT) images, x-ray images, digitalized 3D physical model images, magnetic resonance images, nuclear medicine images, photographic images, and the like. Any type of image format visualizing the tooth and/or the surrounding areas may be potentially acceptable within the context of the present technology.

In some embodiments of the present technology, the imaging device 230 may be implemented as an intra-oral scanner for providing 3D digital models of the teeth of the patient (e.g., 3D representations of the teeth of the patient). Typically, intra-oral scanners have a component that (i) can be received in the oral region, (ii) has a light source for providing light to the oral region requiring imaging, and (iii) has an imaging sensor for capturing images of the oral region. It is contemplated that the intra-oral scanner may comprise an internal computer system that can (i) receive the captured images and (ii) generate digital 3D surface models (for example, in a "mesh" form or in "point cloud" form) of the oral region. This technique provides an alternative to making traditional plaster models of the oral region followed by their digital imaging.

In other embodiments of the present technology, the imaging device 230 may be implemented as a Computed Tomography (CT) scanner for providing CT scan images. Typically, CT scan images are 3D images and provide x-ray level detail of the teeth, soft tissues, nerve pathways and bone. Optionally, other types of CT scanners can be used to provide panoramic, cephalometric or cone beam projections, without departing from the scope of the present technology.

In further embodiments of the present technology, the imaging device 230 may be implemented as any one of or any combination of: an x-ray apparatus for providing x-ray 2D images of the oral region, a magnetic resonance imaging device for providing magnetic resonance images, an ultrasound apparatus for providing ultrasound images of the oral region, and the like. Irrespective of the particular implementation of the imaging device 230, it is contemplated that the imaging device 230 may comprise at least one hardware processor for processing the images and at least one memory component for storing the images.

Alternatively, as contemplated in other embodiments, the imaging device 230 may be a camera for indirect digitization of intraoral anatomy via a replica (i.e., a dental model). In some such embodiments, the replica is obtainable via a dental impression (i.e., a negative mold) made of a material (such as polyvinyl-siloxane) having been imprinted with the shape of the intraoral anatomy it has been applied to. Alternatively, in other embodiments, the digital surface model may be generated via digitizing the dental impression.

The format in which the 3D image is generated by the imaging device 230 and/or acquired by the computer system is not particularly limited. However, as an example, the 3D image may be generated by the imaging device 230 and/or acquired by the computer system in a vast range of file formats (e.g., STL, OBJ, PLY, DICOM, and various software-specific, proprietary formats).

In some non-limiting embodiments of the present technology, the imaging device 230 may comprise an intra-oral scanner enabling to capture direct optical impressions of the at least one of the lower arch form and the upper arch form of the patient.

In a specific non-limiting example, the intraoral scanner can be of one of the types available from MEDIT, CORP. of 23 Goryeodae-ro 22-gil, Seongbuk-gu, Seoul, South Korea. It should be expressly understood that the intraoral scanner can be implemented in any other suitable equipment.

In other non-limiting embodiments of the present technology, the imaging device 230 may comprise a desktop scanner enabling to digitize a mold (not depicted) representing the given configuration of the at least one of the lower arch form and the upper arch form associated with the respective stage of the orthodontic treatment. In this regard, the mold may have been obtained via dental impression using a material (such as a polymer, e.g. polyvinyl-siloxane) having been imprinted with the shape of the intraoral anatomy it has been applied to. In the dental impression, a flowable mixture (i.e., dental stone powder mixed with a liquid in certain proportions) may be flowed such that it may, once dried and hardened, form the replica.

In a specific non-limiting example, the imaging device 230 can be of one of different types of desktop scanners available from Dental Wings, Inc. of 2251, ave Letourneux, Montreal (QC), Canada, H1V 2N9. It should be expressly understood that the desktop scanner can be implemented in any other suitable equipment.

In yet other non-limiting embodiments of the present technology, the imaging device 230 can comprise a 3D laser scanner enabling to obtain a respective point cloud 3D digital model of the at least one of the lower arch form and the upper arch form of the patient—such as by scanning the mold thereof and thus registering three-dimensional coordinates of points representative of the surface of the mold.

In a specific non-limiting example, the 3D laser scanner can be of one of the types available from LASER DESIGN of 5900 Golden Hills Drive, Minneapolis, Minn. 55416. It should be expressly understood that the desktop scanner can be implemented in any other suitable equipment.

In yet other non-limiting embodiments of the present technology, the imaging device 230 may comprise a cone beam computed tomography (CBCT) scanner. Generally speaking, the CBCT scanner comprises software and hardware allowing for capturing data using a cone-shaped X-ray beam by rotating around the subject's head. This data may be used to reconstruct 3D digital models of the following regions of the patient's anatomy: dental (teeth and gum, for example); oral and maxillofacial region (mouth, jaws, and neck); and ears, nose, and throat ("ENT").

In a specific non-limiting example, the CBCT scanner can be of one of the types available from 3Shape, Private Limited Company of Holmens Kanal 7, 1060 Copenhagen, Denmark. It should be expressly understood that the CBCT scanner can be implemented in any other suitable equipment.

Figure 2:
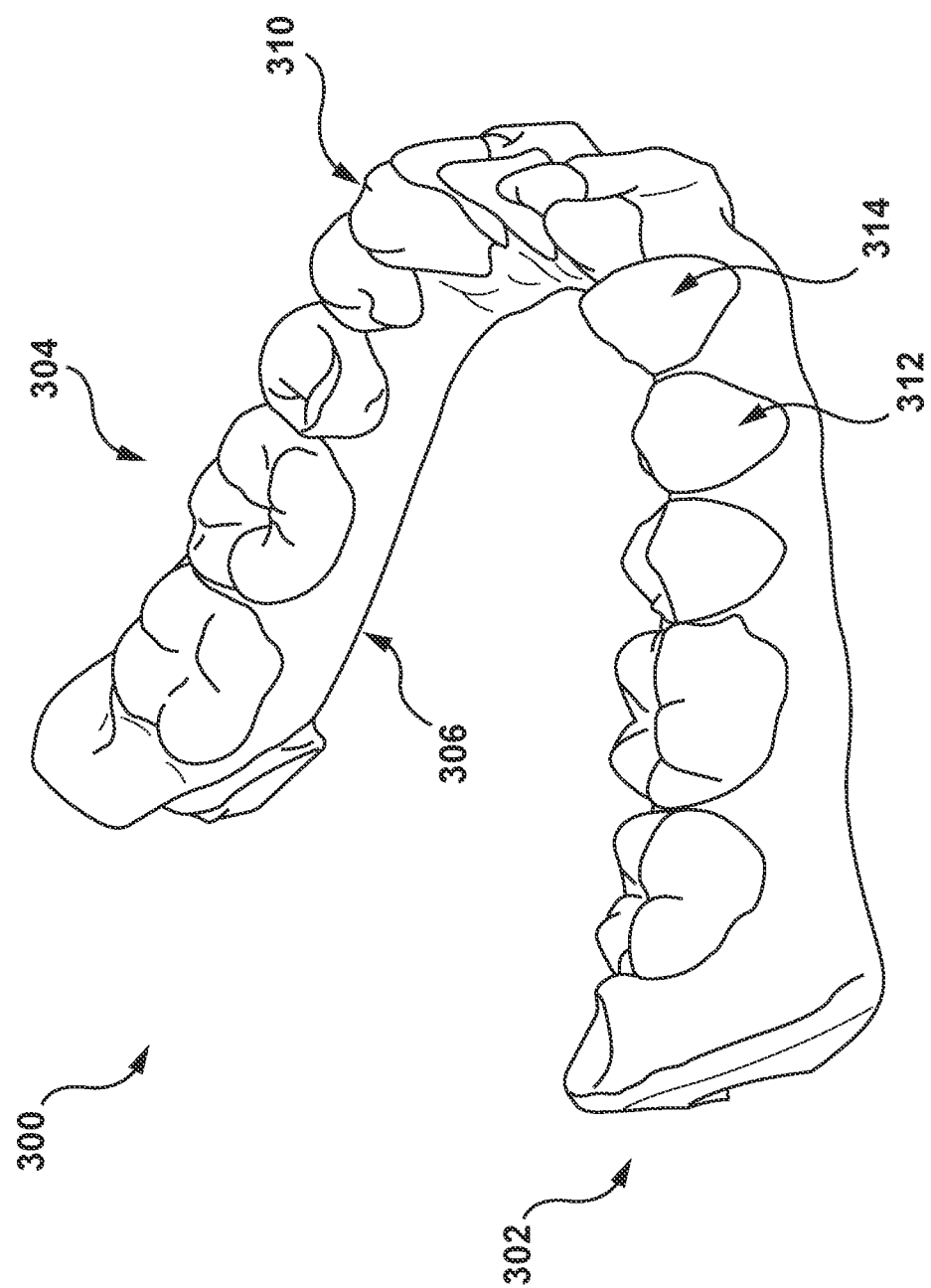
FIG. 2 depicts a 3D image of at least a portion of an oral region of a patient captured by an imaging device, in accordance with various non-limiting embodiments of the present technology.

With reference to FIG. 2, there is depicted a 3D image 300 of at least a portion of an inter-oral region of a patient. More specifically, the 3D image 300 generally shows a lower arch form 302 of the patient including a plurality of lower teeth 310, including a crown portion 304 of each tooth, as well as surrounding tissues 306 (also referred to as gingiva or gums). The plurality of lower teeth 310 include two adjacent teeth: a first tooth 312 and a second tooth 314.

As mentioned above, it is contemplated that the 3D image 300 may be captured by the imaging device 230, implemented as the intra-oral scanner for example. The format in which the 3D image 300 is acquired and/or processed by the imaging device 230 and/or acquired or processed by the computer system 110 is not particularly limited.

In the context of the present technology, it is contemplated that the 3D image 300 is a 3D representation of the lower arch form 302 of the patient. The 3D image 300 can also be represented as a 3D digital model for use in embodiments of the methods described herein. The imaging device 230 may be configured to convert the image data of the 3D image 300 to the 3D digital model, which may be of any type such as a mesh-type 3D model, or a point cloud type 3D model. Alternatively, the image data may be converted to a 3D model in any other way, such as by the processor 202 of the computer system 110

Various non-limiting embodiments of the present technology are directed towards performing digital separation of two adjacent teeth, such as adjacent ones of the plurality of lower teeth 310 of the lower arch form 302 based on the 3D digital model of the adjacent teeth of the patient. In other words, the 3D model is digital in nature. The digital separation of the two adjacent teeth such as the first tooth 312 and the second tooth 314 may model a given IPR procedure in which enamel is removed from one or both of the two adjacent teeth.

Various non-limiting embodiments of the present technology may generate a separation plane and based on the separation plane, various non-limiting embodiments may generate a first cutting plane and a second cutting plane. Further, various non-limiting embodiments may update the 3D digital model by removing elements of the 3D digital model which are between the first and second cutting planes, thereby performing the digital separation of two adjacent teeth. The updated 3D digital model may represent the outer geometry of the two adjacent teeth after the enamel has been removed. Visualization of the updated 3D digital model may assist the orthodontic practitioner to perform the actual IPR process that was modelled, and/or used to plan the orthodontic treatment.

Figure 3:
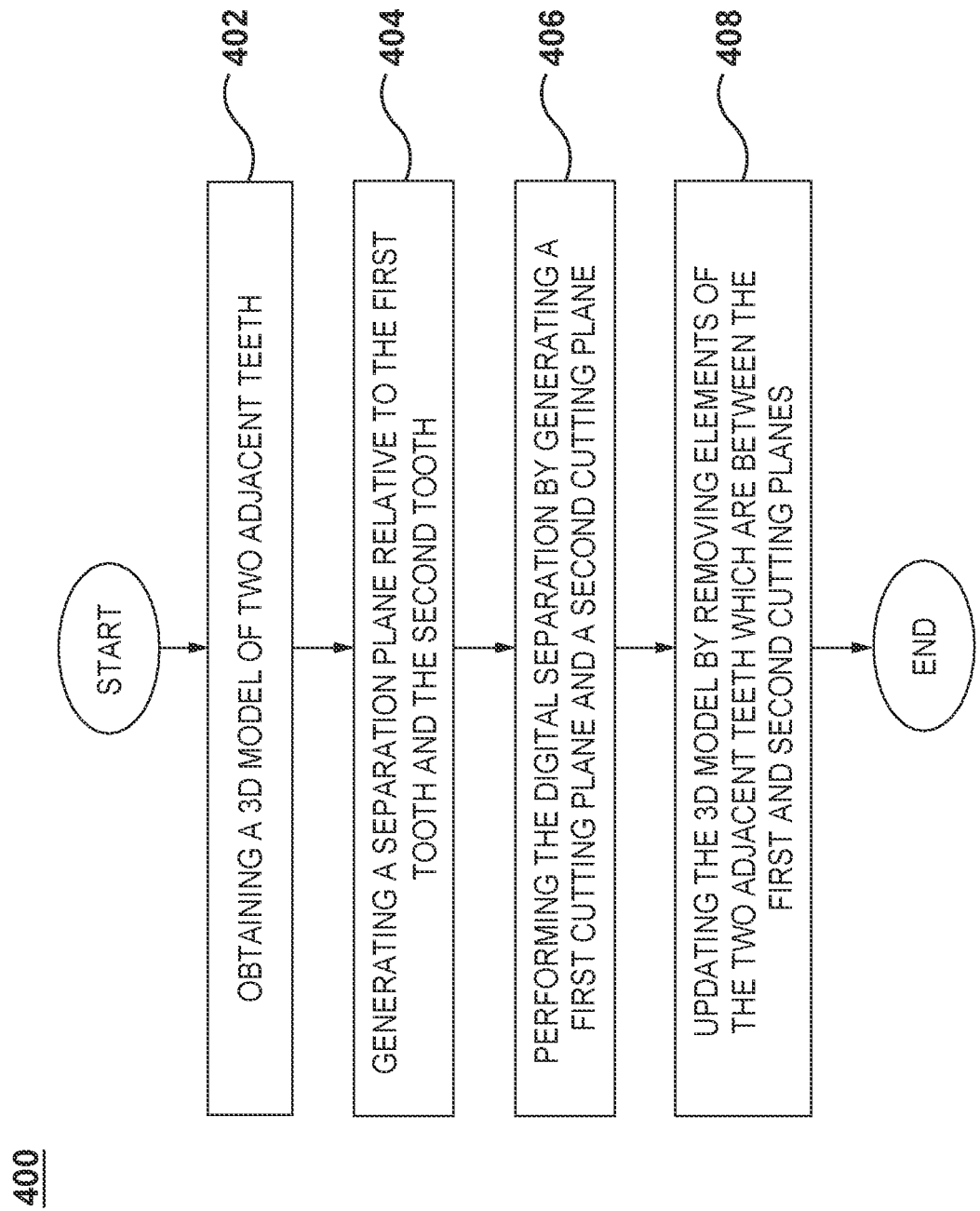
FIG. 3 illustrates a flowchart representing a process corresponding to a method for performing digital separation of two adjacent teeth implemented on the computer system, in accordance with various non-limiting embodiments of the present technology.

With this said, FIG. 3 illustrates a flowchart representing a process corresponding to a method 400 for performing digital separation of two adjacent teeth, such as adjacent teeth of the lower arch form 302, implemented by a computer system such as the computer system 110, in accordance with various non-limiting embodiments of the present technology.

STEP 402: Obtaining a 3D Model of Two Adjacent Teeth

The method 400 commences at step 402, where the processor 202 associated with the computer system 110 obtains the 3D digital model of at least two adjacent teeth, such as two adjacent teeth of the lower arch form 302 of FIG. 2. As such, the 3D digital model may include a first set of elements comprising first tooth elements representing an outer geometry of the first tooth 312 and second tooth elements representing an outer geometry of the second tooth 314.

In various non-limiting embodiments, the processor 202 may be configured to obtain the 3D digital model from the imaging device 230. In certain embodiments, the processor 202 may be configured to generate the 3D digital model from the image data obtained from the imaging device 230 or may be configured to retrieve the 3D digital model from a memory. In other non-limiting embodiments, the imaging device 230 may be configured to generate the 3D digital model of the two adjacent teeth by any suitable technique know to a person skilled in the art.

Furthermore, in certain embodiments, the 3D digital model of the two adjacent teeth may represent the crown portions 304 of the two adjacent teeth which have been separated from the surrounding tissues 306. In this respect, the method 400 may comprise the processor 202, segmenting the 3D digital model of the lower arch form 302, so as to isolate the crown portions 304 of the first tooth 312 and the second tooth 314 from other teeth of the lower arch form 302 and from the surrounding tissues 306 of the lower arch form 302.

How the processor 202 is configured to isolate the crown portions 304 of the two adjacent teeth is not limited; and, in some non-limiting embodiments of the present technology, the processor 202 can be configured to apply one or more automatic tooth segmentation approaches, such as the methods described in a co-owned U.S. Pat. No. 10,916,068-B1 issued on Feb. 9, 2021, entitled "SYSTEMS AND METHODS FOR PLANNING AN ORTHODONTIC TREATMENT", content of which is incorporated herein by reference in its entirety.

Alternatively, the 3D digital model of the crown portions of the two adjacent teeth may be obtained by the imaging device 230 or the processor 202 selecting the crown portions from the image data and converting only those portions to the 3D digital model.

Figure 4A:
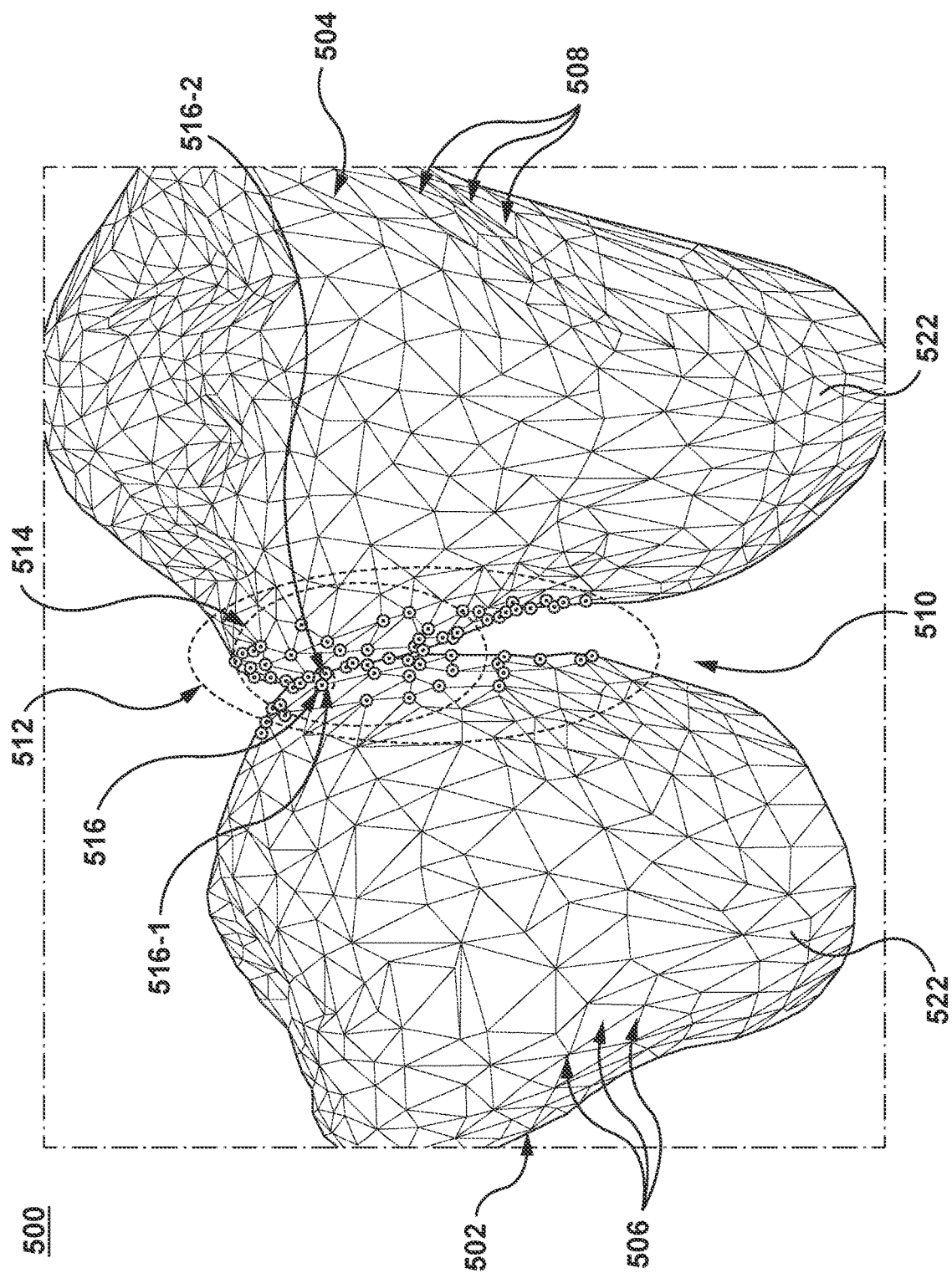
FIG. 4A illustrates a 3D digital model representing a first tooth and a second tooth being represented as a polygon mesh, in accordance with various non-limiting embodiments of the present technology.

FIG. 4A illustrates a 3D digital model 500 representing outer geometries of crown portions of a first tooth 502 and a second tooth 504, such as the crown portions 304 of the first tooth 312 and the second tooth 314 of the lower arch form 302 of FIG. 2. The 3D digital model 500 is represented as a triangular polygon mesh, in accordance with various non-limiting embodiments of the present technology.

The polygon mesh may be a plurality of vertices, edges and faces that defines the outer geometry of crown portions of the first tooth 502 and the second tooth 504. Each vertex of the vertices is a point in space, such as 3D space. Each vertex may be defined by a Cartesian coordinate or by any other suitable coordinate system representing a spatial location of the vertex. A given edge of the plurality of vertices connects two vertices. A given face of the plurality of faces can be a closed set of edges. The faces may have a polygon configuration such as a triangle (triangle mesh), a quadrilateral (quads), or other simple polygons (n-gons). The polygons may be convex or concave. In the context of embodiments of the present technology, first tooth elements 506 may comprise a plurality of mesh vertices representing the outer geometry of the first tooth 502 and second tooth elements 508 may comprise a plurality of mesh vertices representing the outer geometry of the second tooth 504. Together, the first tooth elements 506 and the second tooth elements 508 may be referred to as a first set of elements 522.

FIG. 5 illustrates another embodiment of the 3D digital model 500, 3D digital model 540. In the 3D digital model 540 of FIG. 5, crown portions of the first tooth 502 and the second tooth 504 are represented as a 3D point cloud instead of a mesh, in accordance with various non-limiting embodiments of the present technology.

In certain non-limiting embodiments, the imaging device 230 or the processor 202 may be configured to generate the 3D digital model 540 by selecting a portion from the 3D image 300 (as shown in FIG. 2) representing an outer geometry of the crown portions of the two adjacent teeth, or by segmenting the 3D image or the image data of the lower arch form 302 to isolate the crown portions of the two adjacent teeth from the surrounding tissues and other teeth. Alternatively, the processor 202 may be configured to convert the 3D digital model 500 comprising a mesh to the 3D digital model comprising the 3D point cloud.

A 3D point cloud is a set of 3D points in space. The 3D points are spaced relative to each other in the space to represent the outer geometry of the crown portions of the first tooth 502 and the second tooth 504. Each 3D point may be defined by a set of Cartesian coordinates or coordinates of any other suitable coordinate system representing a spatial location of the 3D point in the space. The 3D point cloud representation differs from that of the polygon mesh representation, in that the 3D point cloud representation may include only information comparable to the vertices but not the surface polygons and edges. First tooth elements 546 may comprise 3D points representing the outer geometry of the crown portion of the first tooth 502 and second tooth elements 548 may comprise 3D points representing the outer geometry of the crown portion of the second tooth 504. Together, the first tooth elements 546 and the second tooth elements 548 may be referred to as a first set of elements 524.

Figure 6:
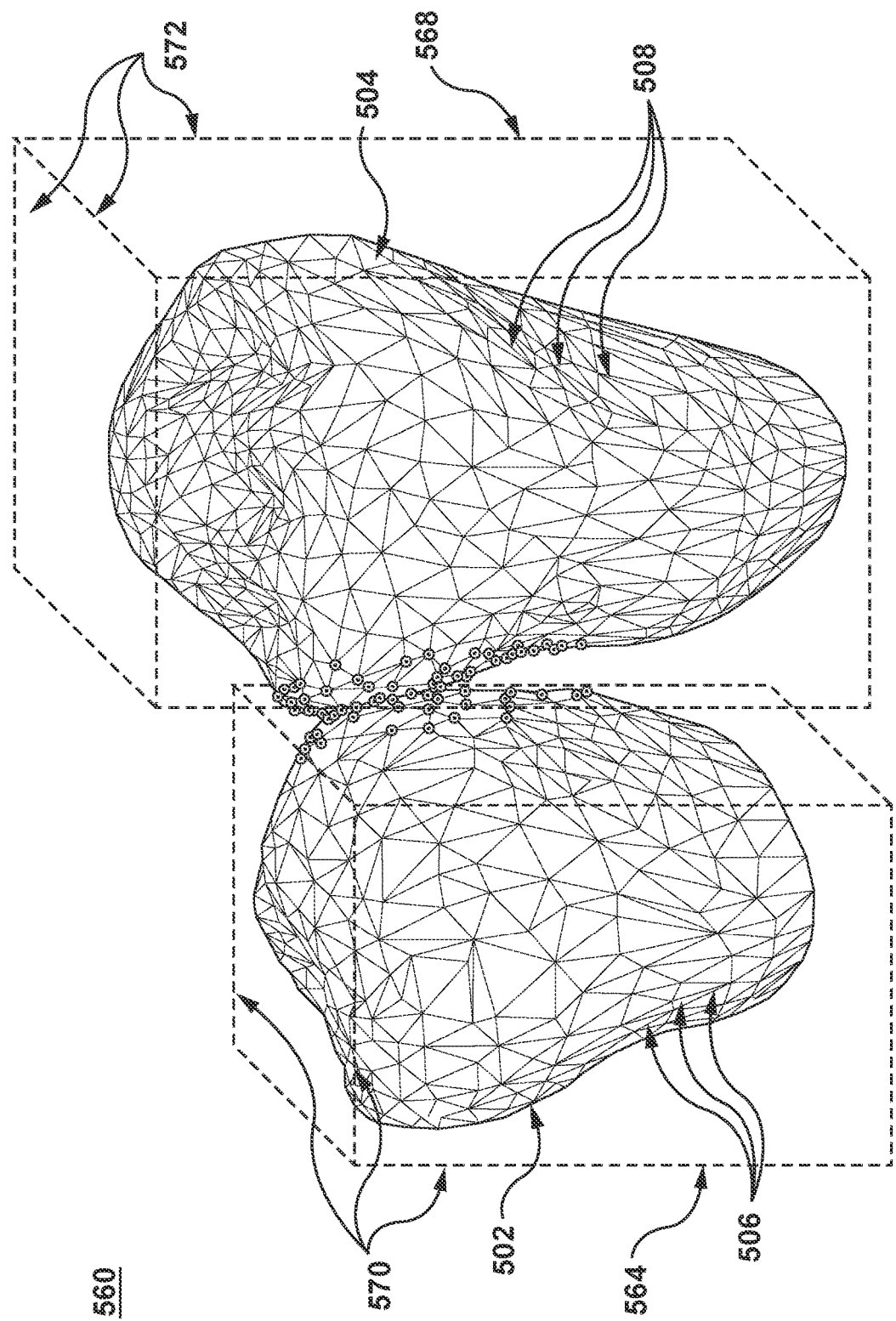
FIG. 6 illustrates another 3D digital model representing the first tooth and the second tooth being represented as axis-aligned bounding box (AABB), in accordance with various non-limiting embodiments of the present technology.

FIG. 6 illustrates another embodiment of the 3D digital model 500, 3D digital model 560 representing the first tooth 502 and the second tooth 504. The 3D digital model 560 differs from the 3D digital model 500 in that there are provided axis-aligned bounding boxes (AABB) around the mesh representations of the first tooth 502 and the second tooth 504, in accordance with various non-limiting embodiments of the present technology. The axis-aligned bounding boxes may comprise a first bounding box 564 around the first tooth 502 and a second bounding box 568 around the second tooth 504.

In certain non-limiting embodiments, the imaging device 230 or the processor 202 may be configured to generate the first bounding box 564 around the first tooth 502 and the second bounding box 568 around the second tooth 504. In certain embodiments the first bounding box 564 and the second bounding box 568 may be generated based on the 3D digital model 500. In other words, the first bounding box 564 may be generated around the plurality of mesh vertices (first tooth elements 506) associated with the outer geometry of the crown portion of the first tooth 502. Similarly, the second bounding box 568 may be generated around the plurality of mesh vertices (second tooth elements 508) associated with the outer geometry of the crown portion of the second tooth 504.

Each of the first bounding box 564 and the second bounding box 568 generally has a rectangular configuration having an elongate axis which is aligned with an axes of a coordinate system of the first tooth elements 506 and the second tooth elements 508. In some non-limiting embodiments, the elongate axis of the rectangular configuration of the first bounding box 564 and the second bounding box 568 may be aligned with axes of the first tooth 502 and the second tooth 504 respectively. The first tooth elements 506 associated with the first tooth 502 may be enclosed in the first bounding box 564. Similarly, the second tooth elements 508 associated with the second tooth 504 may be enclosed in the second bounding box 568.

Further, the first bounding box 564 may be defined by a first set of AABB vertices 570 and the second bounding box 568 is defined by a second set of AABB vertices 572. The first set of AABB vertices 570 may enclose the first tooth elements 506 representing the crown portion of the first tooth 502. The second set of AABB vertices 572 may enclose the second tooth elements 508 representing the crown portion of the second tooth 504.

Figure 7:
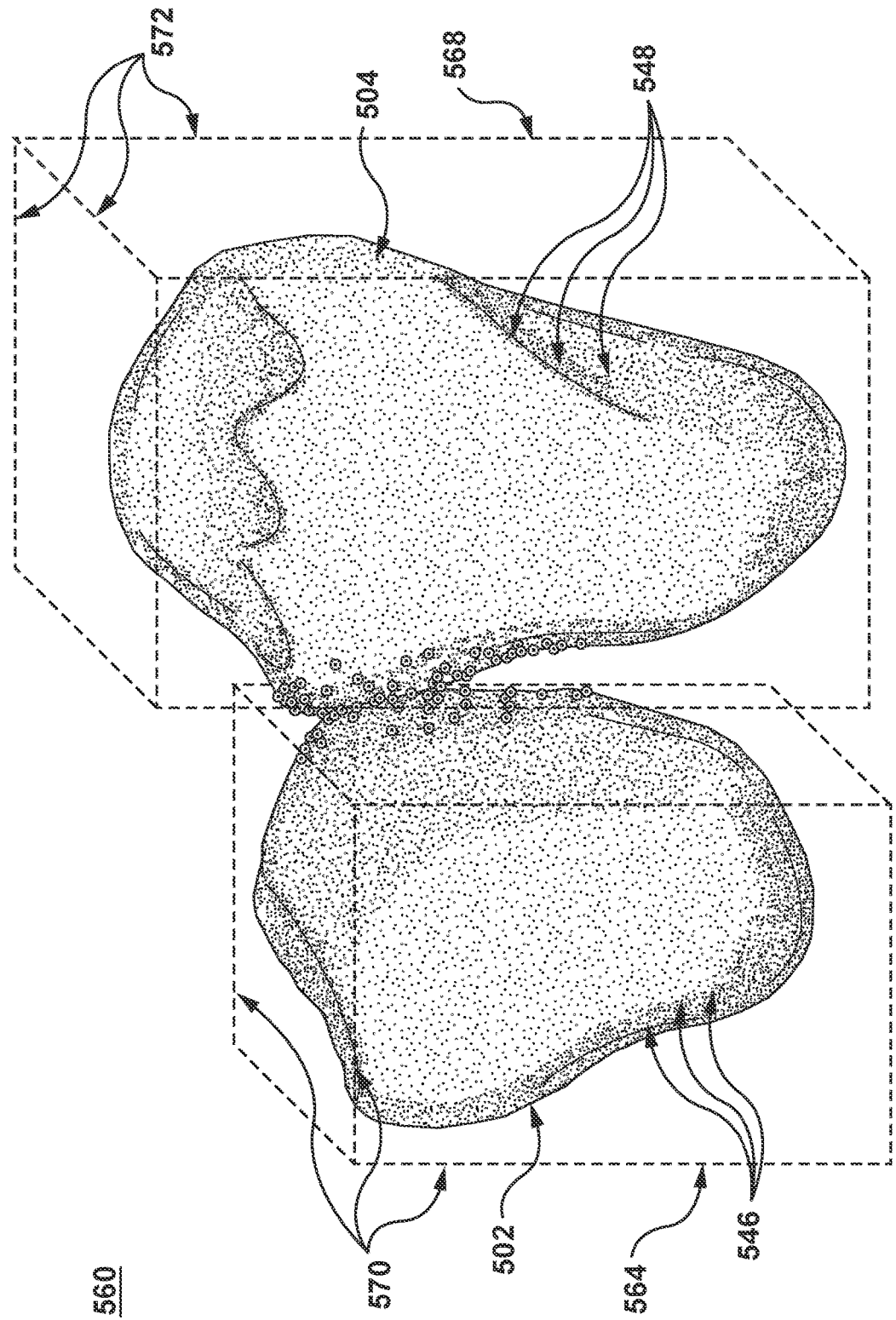
FIG. 7 illustrates yet another 3D digital model representing the first tooth and the second tooth being represented as AABB, in accordance with various non-limiting embodiments of the present technology.

FIG. 7 illustrates yet another embodiment of the 3D digital model 550, 3D digital model 580 representing the first tooth 502 and the second tooth 504. The 3D digital model 580 differs from that of the 3D digital model 540 in that there are provided axis-aligned bounding boxes (AABB) around the 3D points (first tooth elements 546 and second tooth elements 548) representing the first tooth 502 and the second tooth 504, in accordance with various non-limiting embodiments of the present technology. The axis-aligned bounding boxes may comprise the first bounding box 564 around the first tooth 502 and the second bounding box 568 around the second tooth 504.

In certain embodiments the first and second bounding box 564, 568 may be generated based on the 3D digital model 540. In other words, the first bounding box 564 may be generated around the first tooth elements 546 associated with the outer geometry of the crown portion of the first tooth 502. Similarly, the second bounding box 568 may be generated around the second tooth elements 548 associated with the outer geometry of the crown portion of the second tooth 504.

In certain embodiments, the imaging device 230 may identify and isolate the two adjacent teeth from the 3D image 300 of the lower arch form 302 and may generate a suitable 3D digital model therefrom (e.g., the 3D digital model 500, 540, 560, and/or 580) representing the crown portions of the two adjacent teeth. In other embodiments, the imaging device 230 may generate a suitable 3D digital model (e.g., the 3D digital model 500, 540, 560, and/or 580) representing the lower arch form 302, and isolate the two adjacent teeth therefrom.

It will be appreciated that, although the depicted and described embodiments refer to the lower arch form 302, the present technology can equally be applied to the upper arch form, or to portions of the lower arch form or the upper arch form. Furthermore, the first tooth 502 and the second tooth 504 may differ from those illustrated herein, and may refer to any teeth of the patient for which digital separation is required. It will also be appreciated the 3D digital model (e.g., the 3D digital model 500, 540, 560, and/or 580) may be based on the plurality of lower teeth 310 of the lower arch form 302 after they have been moved through a modelled or actual orthodontic treatment. In this respect, in cases of a modelled orthodontic treatment, the first tooth 502 and the second tooth 504 may be overlapping one another in the 3D digital model. In other words, portions of the 3D digital model representing crown portions of the first tooth and the second tooth may be overlapping each other in 3D space.

The first tooth 502 and the second tooth 504 may be identified in any suitable manner. For example, the first tooth 502 and the second tooth 504 may be identified manually by the orthodontic practitioner using an interactive user interface of the computer system 110 for example. In other examples, the two adjacent teeth to which embodiments of the present technology may be applied, may be selected automatically or semi-automatically through digital identification of a given tooth.

In certain embodiments, the orthodontic practitioner may select the specific 3D digital model type to represent the two adjacent teeth (e.g., the 3D digital model 500, 540, 560, and/or 580) using the interactive user interface for example, or the 3D digital model type may be selected based on one or more predetermined factors.

It is contemplated that how the two adjacent teeth have been selected to be represented as 3D digital model 500 and how the two adjacent teeth have been represented as the 3D digital models (e.g., the 3D digital model 500, 540, 560, and/or 580) should not limit the scope of the present technology.

STEP 404: Generating a Separation Plane Relative to the First Tooth and the Second Tooth The method 400 proceeds to step 404, where the processor 202 associated with the computer system 110 generates a separation plane relative to the first tooth 502 and the second tooth 504, such as the first tooth 502 and the second tooth 504.

Referring to FIG. 4A, in order to generate the separation plane, in certain non-limiting embodiments, the processor 202 may be configured to determine or obtain a separation zone 510 associated with the two adjacent teeth, such as the first tooth 502 and the second tooth 504.

In certain embodiments, the separation zone 510 may be referred to as portions of the outer geometries of each of the two adjacent teeth to which the IPR process could be applied. The separation zone 510 may include an interdental region of the two adjacent teeth, such as the first tooth 502 and the second tooth 504. The separation zone 510 may be predetermined by defining, for example, one or more of the following aspects of the separation zone 510: an area of the separation zone 510, a volume of the separation zone 510, a distance of a periphery of the separation zone 510 from an axis of each of the two adjacent teeth.

In the example of FIG. 4A in which the two adjacent teeth are not overlapping with each other, i.e. they are spaced from each other, the separation zone 510 may include portions of the outer geometry of the first tooth 502 and the second tooth 504 facing each other. In other words, the separation zone 510 may be defined by respective subsets of the first tooth elements 506 and the second tooth elements 508 defining the outer geometries of the first tooth 502 and the second tooth 504.

In some other examples (not depicted), in which the two adjacent teeth, such as the first tooth 502 and the second tooth 504 overlap with each other in the 3D digital model 500, the separation zone 510 may include the overlapping portions of the two adjacent teeth, such as the first tooth 502 and the second tooth 504.

Having determined or obtained the separation zone 510 associated with the two adjacent teeth, such as the first tooth 502 and the second tooth 504, the processor 202 may be configured to identify a second set of elements 512 associated with the separation zone 510 of the two adjacent teeth, such as the first tooth 502 and the second tooth 504.

It is contemplated that the second set of elements 512 may be defined relative to the type of the 3D digital model (e.g., the 3D digital model 500, 540, 560, and/or 580) representing the crown portions of the first tooth 502 and the second tooth 504 and being used to generate the separation plane.

For example, with respect to FIG. 4A in which the 3D digital model is the 3D digital model 500, then the second set of elements 512 may be defined as a subset of the mesh vertices associated with the first tooth 502 and the second tooth 504 which are located in the separation zone 510. In other words, the second set of elements 512 comprises a subset of the first tooth elements 506 and the second tooth elements 508 of the 3D digital model 500.

Without limiting the scope of present technology, in another example, if the associated 3D digital model is the 3D digital model 540 (as shown in FIG. 5), the second set of elements 512 may be defined as a subset of the 3D points associated with the first tooth 502 and the second tooth 504 which are located in the separation zone 510. In other words, the second set of elements 512 comprises a subset of the first tooth elements 546 and the second tooth elements 548.

Figure 4B:
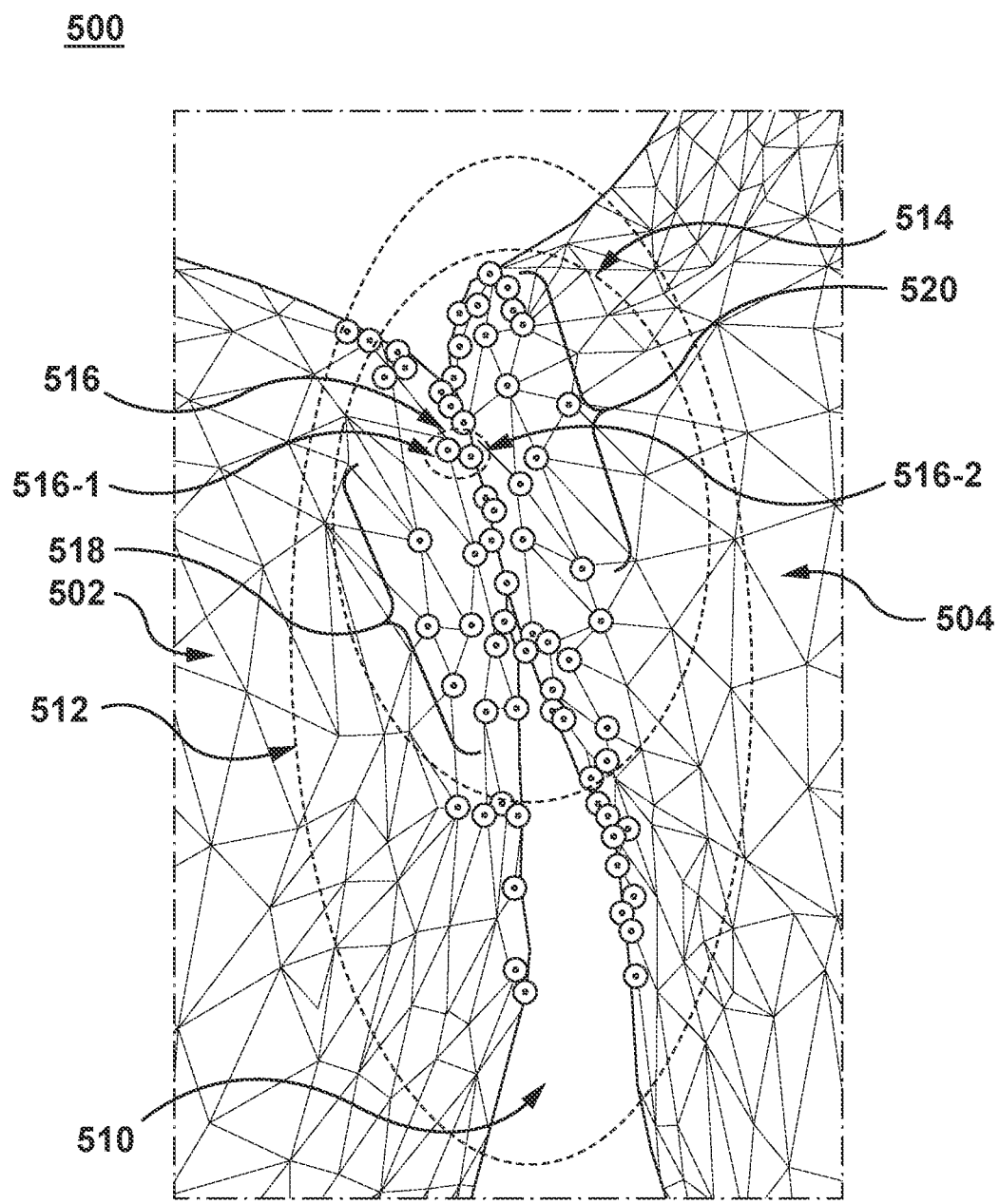
FIG. 4B illustrates a magnified version of the 3D digital model, in accordance with various non-limiting embodiments of the present technology.

Once, the second set of elements 512 is obtained, the processor 202 may be configured to identify a third set of elements 514 which are a subset of the second set of elements 512. In certain embodiments, the third set of elements 514 is identified by identifying those first tooth elements 506, 546 within the second set of elements 512 which are within a threshold distance from the second tooth elements 508, 548. In other words and as shown in FIG. 4B, the third set of elements 514 may include a first portion 518 of the first tooth elements 506, 546 in the separation zone 510 being within a threshold distance from a second portion 520 of the second tooth elements 508, 548 in the separation zone 510.

Thus, by virtue of identifying the second set of elements 512, computational burden on the processor 202 may be reduced. As, in this case the processor 202 may have to process only the second set of elements 512 instead of all of the first tooth elements 506, 546 and the second tooth elements 508, 548 associated with the first tooth 502 and the second tooth 504.

In certain non-limiting embodiments, the threshold distance may represent a separation distance between the first tooth 502 and the second tooth 504. In various non-limiting embodiments, the threshold distance may depend on existing overlap or separation between the first tooth 502 and the second tooth 504.

By way of example, the threshold distance may be a predetermined distance.

If the outer geometries of the first tooth 502 and the second tooth 504 in the 3D digital model 500 overlap with each other, the processor 202 may identify the third set of elements 514 by identifying element pairs, such as, element pair 516, of the first tooth 502 and the second tooth 504 (As shown in FIG. 4B). The element pair 516 may comprise a first element 516-1 associated with the first tooth 502 and a second element 516-2 associated with the second tooth 504. In certain embodiments, the element pair 516 is selected in a manner that a distance between the first element 516-1 and the second element 516-2 is within the predetermined distance. In other words, the distance between the first element 516-1 and the second element 516-2 is less than or equal to the predetermined distance.

In various non-limiting embodiments, the processor 202 may be configured to identify all the element pairs in the second set of elements 512 such that the distance between the first tooth elements 506, 546 and the second tooth elements 508, 548 of the element pairs is within the predetermined distance.

In various non-limiting embodiments, the predetermined distance may be set by the orthodontic practitioner using the interactive user interface. In other embodiments, the processor 202 may be configured to set the predetermined distance based on the 3D digital model (e.g., the 3D digital model 500, 540, 560, and/or 580). It is to be noted that how the predetermined distance is set should not limit the scope of the present technology.

In yet another non-limiting embodiment, the threshold distance may be equal to a summation of a shortest distance between any two elements of the first tooth elements 506, 546 and the second tooth elements 508, 548 and the predetermined distance. This may apply, for example, in scenarios where the outer geometries of of the first tooth 502 and the second tooth 504 do not overlap with each other.

Figure 8:
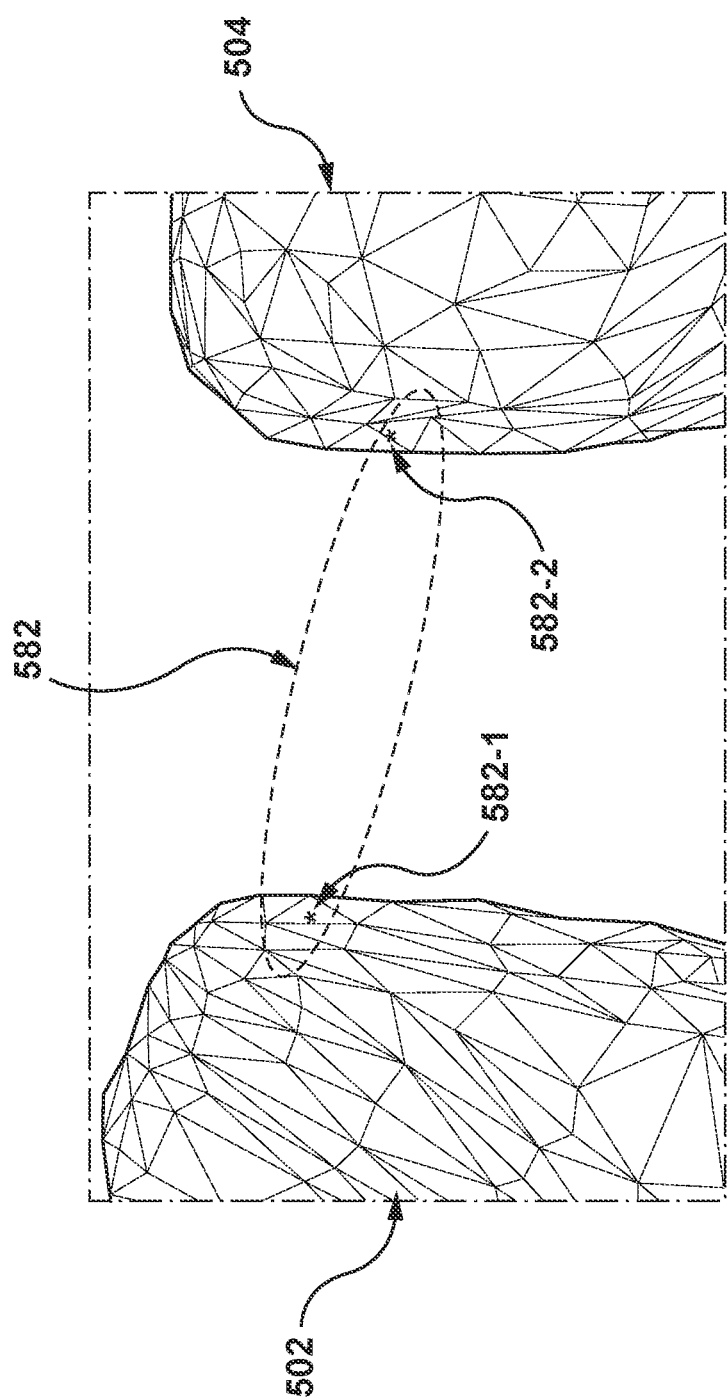
FIG. 8 illustrates a representative scenario where the first tooth and the second tooth do not overlap with each other, in accordance with various non-limiting embodiments of the present technology.

FIG. 8 illustrates a representative scenario where the first tooth 502 and the second tooth 504 do not overlap with each other, in accordance with various non-limiting embodiments of the present technology. In certain non-limiting embodiments, if the outer geometries of the first tooth 502 and the second tooth 504 do not overlap with each other, the processor 202 may identify the third set of elements 514 by identifying a closest element pair, such as, element pair 582, of the first tooth 502 and the second tooth 504. The element pair 582 may comprise a first element 582-1 associated with the first tooth elements 506, 546 and a second element 582-2 associated with the second tooth elements 508, 548. In certain embodiments, the element pair 582 may be selected based on a shortest distance between any two elements of the first tooth elements 506, 546 and the second tooth elements 508, 548.

In certain non-limiting embodiments, the processor 202 may be configured to compute a shortest distance between the first tooth elements 506, 546 and the second tooth elements 508, 548 in the second set of elements 512. The processor 202 may be configured to identify the two elements having a shortest distance among all the first tooth elements 506, 546 and the second tooth elements 508, 548 in the second set of elements 512. In FIG. 8, such elements have been illustrated as the first element 582-1 and the second element 582-1 and the element pair is represented as element pair 582.

Based on the shortest distance associated with the element pair 582, the processor 202 may be configured to determine the third set of elements 514. The third set of elements 514 may include those element pairs which are separated by a distance less than equal to the summation of the shortest distance and the predetermined distance.

In various non-limiting embodiments, the processor 202 may be configured to compute the shortest distance using any suitable technique, such as, using a bounding volume hierarchy (BVH) structure, converting the outer geometry of at least one of the first tooth 502 and the second tooth 504 into a distance field data structure, or reducing a dimensionality of the first tooth elements 506, 546 and the second tooth elements 508, 548 in the 3D digital model (e.g., the 3D digital model 500, 540, 560, and/or 580) from 3D Cartesian coordinates to 2D UV Cartesian coordinates.

In various non-limiting embodiments, the processor 202 may rely on BVH structure for shortest distance computation in case the 3D digital model (e.g., the 3D digital model 560, and/or 580) is based on AABB.

In various non-limiting embodiments, the distance field data structure may include precomputed shortest distances from the first tooth elements 506, 546 to the second tooth elements 508, 548.

The precomputed shortest distances may be embedded in the 3D digital model (e.g., the 3D digital model 500, 540, 560, and/or 580). The shortest distance from the first tooth elements 506, 546 to the second tooth elements 508, 548 may be calculated as interpolation of a few surrounding precomputed vertices/3D points. As previously discussed, the various elements, such as mesh vertices and 3D points, representing the 3D digital model (e.g., the 3D digital model 500, 540, 560, and/or 580) may have a spatial representation using Cartesian coordinates or any other suitable coordinate system. Based on the coordinates of the elements, the processor 202 may be configured to compute distances to some surrounding vertices/3D points.

Representing at least one of the first tooth 502 and the second tooth 504 as distance field aims to perform Time-to-Memory trade-off and improve the performance of the processor 202 on crucial computation phase. The distance fields may be computed for the first tooth 502 and the second tooth 504 beforehand as a preliminary data preparation step.

In various non-limiting embodiments, if various elements, such as mesh vertices, 3D points, representing the 3D digital model (e.g., the 3D digital model 500, 540, 560, and/or 580) have been represented as 3D Cartesian coordinates, the processor 202 may be configured to reduce the dimensionality and perform voxelization of the first tooth elements 506, 546 and the second tooth elements 508, 548 in the 3D digital model (e.g., the 3D digital model 500, 540, 560, and/or 580) from 3D Cartesian coordinates to 2D UV Cartesian coordinates. This may be an alternative technique for measuring distances between vertices/3D points of the outer geometry of the first tooth 502 or the second tooth 504 and arbitrary vertices/3D points.

To do so, for a given pair of teeth, the processor 202 may be configured to convert the coordinate system from original 3D Cartesian to 2D Cartesian UVD, where D axis is parallel to the vector connecting a center of the first tooth 502 and the second tooth 504. The processor 202 may be configured to define a uniform 2D grid at UV plane, each grid having a step size of 's'. The uniform 2D grid may represent the 3D digital model (e.g., the 3D digital model 500, 540, 560, and/or 580). The uniform 2D grid may include a plurality of 2D grid cells such that a given 2D grid cell of the plurality of 2D grid cells corresponds to a respective one of the elements of the 3D digital model (e.g., the 3D digital model 500, 540, 560, and/or 580).

Further, each 2D grid cell (i,j) of the plurality of 2D grid cells may represent two intervals on U and V axis correspondingly:

$$u \in [s*i, (s+1)*i] \quad (1)$$

$$v \in [s*j, (s+1)*j] \quad (2)$$

For the purpose of simplicity, the transformation functions may be represented as following:

$$UV \text{ to } IJ(u,v) \to (i,j) \quad (3)$$

$$IJ \text{ to } UV(i,j) \to (u,v) \quad (4)$$

Going forward, the processor 202 may be configured to assign, to each one of the plurality of 2D grid cells, a first depth value (such as a MinDepth value) and a second depth value (such as a MaxDepth value), the second depth value being greater than the first depth value.

The MinDepth and MaxDepth values may aggregate D axis of the vertices/3D points matching the 2D grid cell. The MinDepth and MaxDepth values may be represented as:

$$\text{MinDepth}(i,j) = (d_k : UV \text{ to } IJ(u_k, v_k) == (i,j)) \quad (5)$$

$$\text{MaxDepth}(i,j) = (d_k : UV \text{ to } IJ(u_k, v_k) == (i,j)) \quad (6)$$

The following condition is used to test an arbitrary vertex/3D point on the outer geometry of the first tooth 502 or the second tooth 504:

$$(x,y,z) \to (u,v,d) \quad (7)$$

$$(i,j) = UV \text{ to } IJ(u,v) \quad (8)$$

$$\text{MinDepth}(i,j) < d < \text{MaxDepth}(i,j) \quad (9)$$

Based on the MinDepth and MaxDepth values, the processor 202 may be configured to compute the shortest distance between two elements of the 3D digital model (e.g., the 3D digital model 500, 540, 560, and/or 580) of the first tooth 502 and the second tooth 504.

The following expressions may provide an estimate of the shortest distance between two elements of the 3D digital model (e.g., the 3D digital model 500, 540, 560, and/or 580):

$$(x,y,z) \to (u,v,d) \quad (10)$$

$$(i,j) = UV \text{ to } IJ(u,v) \quad (11)$$

$$\text{Shortest Distance} = \text{Max}(\text{MinDepth}(i,j) - d, d - \text{MaxDepth}(i,j)) \quad (12)$$

It is to be noted that the shortest distance as computed above is an approximate shortest distance as the tooth surface convexity is not taken into account. However, Developers have found that such methods suffice to determine the separation plane. In addition, such technique may improve the performance of the processor 202 on crucial computation phase.

Figure 9:
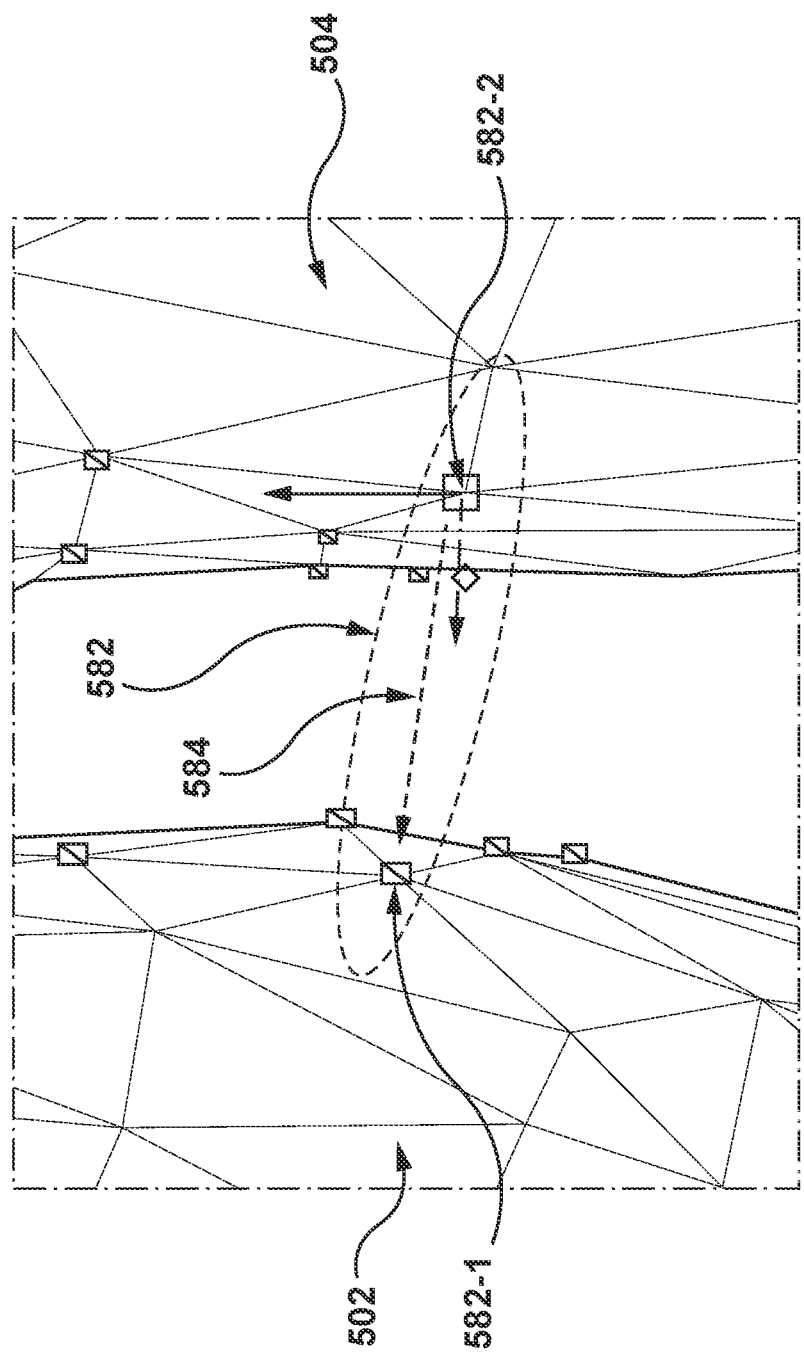
FIG. 9 illustrates a shortest distance computed between the first element and the second element, in accordance with various non-limiting embodiments of the present technology.

FIG. 9 illustrates a shortest distance 584 between the first element 582-1 and the second element 582-2 computed based on any suitable technique as discussed above, in accordance with various non-limiting embodiments of the present technology. Based on the shortest distance 584, the processor 202 may be configured to determine the third set of elements 514. The third set of elements 514 may include those element pairs which are separated by a distance less than equal to the summation of the shortest distance and the predetermined distance. Each of the element pair (e.g., the element pair 582) may include the first element 582-1 associated with the first tooth 502 and the second element 582-2 associated with the second tooth 504.

In certain non-limiting embodiments, the processor 202 may be configured to determine the separation plane based on the identified third set of elements 514. In various non-limiting embodiments, a given element in the third set of elements 514 may be attributed with a scalar value of a shortest distance from the given element to the outer geometry of the adjacent tooth surface. In various nonlimiting embodiments, the processor 202 may ignore the elements in the third set of elements 514 which are inside the adjacent tooth geometry.

In various non-limiting embodiments, for the purpose of understanding the mechanism of generating the separation plane, one tooth of the pair of the adjacent teeth, such as the first tooth 502, may be referred as positive tooth 502, and the other tooth, such as the second tooth 504 may be referred as negative tooth 504.

The processor 202 may negate the attributed scalar values of the shortest distances associated the elements of the negative tooth 504 in the third set of elements 514. In other words, the processor 202 may multiply the attributed scalar values by −1.

In various non-limiting embodiments, a mathematical equation of the separation plane may be described as:

$$ax + by + cz + d = 0 \quad (13)$$

Where a, b, c, and d are equation parameters. In various non-limiting embodiments, the processor 202 may be configured to determine the separation plane in accordance with the third set of elements 514. In particular, by performing a planar fitting of 3D Cartesian coordinates of the third set of elements 514 and solving a linear regression. A person skilled in the art would readily understand the process of generating a plane based on 3D points by solving the linear regression. In addition, for the ith element pair in the third set of elements 514, the processor 202 may be configured to minimize an error during planar fitting by using the following equation:

$$\Sigma_i (ax_i + by_i + cz_i + d - \text{Shortest Distance}_i)^2 \to 0 \quad (14)$$

where: $a^2 + b^2 + c^2 = 1$

Figure 10:
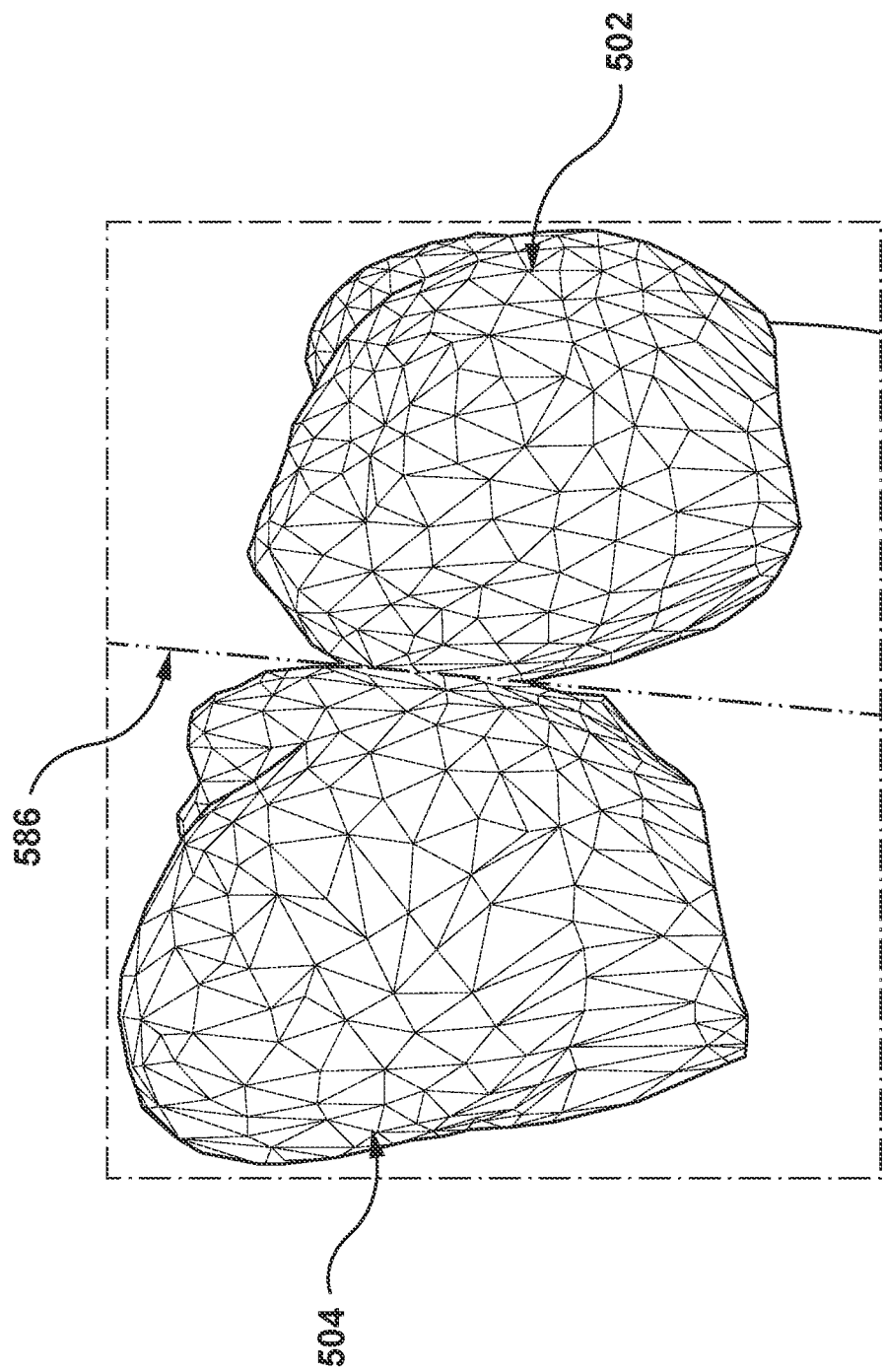
FIG. 10 illustrates a separation plane generated between the first tooth and the second tooth, in accordance with various non-limiting embodiments of the present technology.

FIG. 10 illustrates a separation plane 586 generated between the first tooth 502 and the second tooth 504, in accordance with various embodiments of the present technology.

STEP 406: Performing the Digital Separation by Generating a First Cutting Plane and a Second Cutting Plane The method 400 proceeds to step 406, where the processor 202 performs the digital separation by generating a first cutting plane and a second cutting plane.

Figure 11:
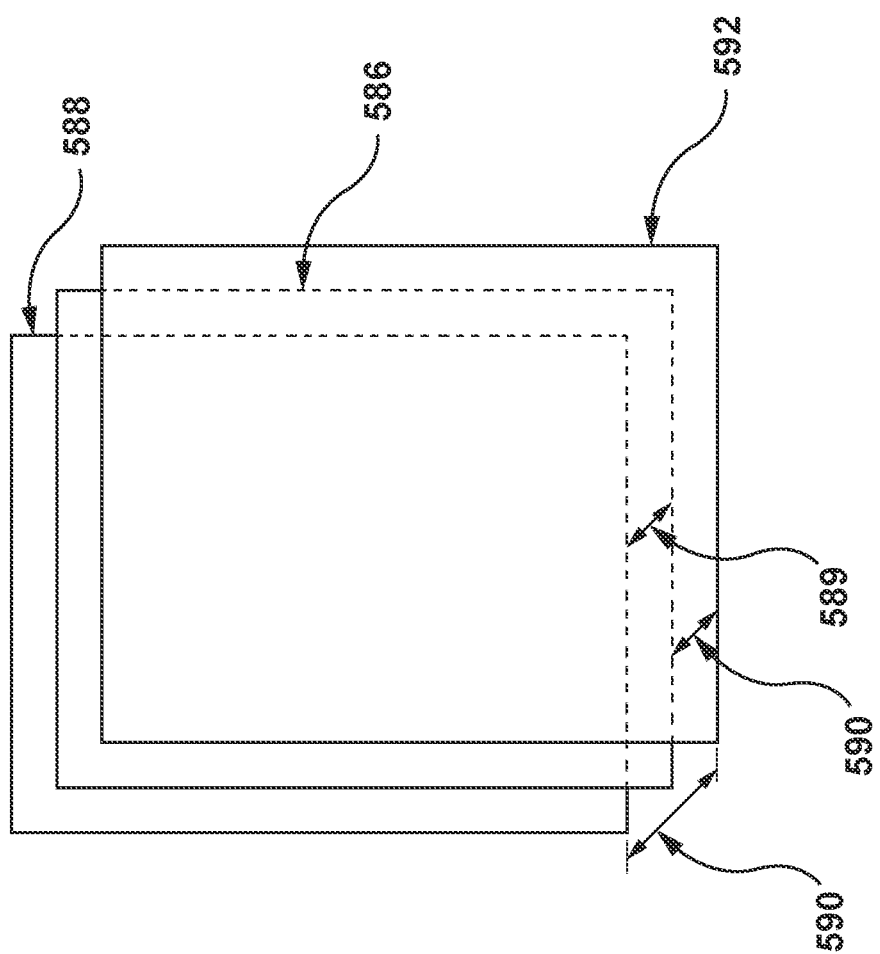
FIG. 11 illustrates the separation plane, a first cutting plane and a second cutting plane, in accordance with various non-limiting embodiments of the present disclosure.

FIG. 11 illustrates the separation plane 586, a first cutting plane 588 and a second cutting plane 592 generated by the processor 202, in accordance with various non-limiting embodiments of the present disclosure. In certain non-limiting embodiments, the first cutting plane 588 may be generated parallel to the separation plane 586 and spaced therefrom towards one of the two adjacent teeth (e.g., the first tooth 502) by a first separation distance 589, and the second cutting plane 592 being parallel to the separation plane 586 and spaced therefrom towards the other of the two adjacent teeth (e.g., the second tooth 504) by a second separation distance 590.

In various non-limiting embodiments, the first cutting plane 588 and the second cutting plane 592 may be generated in addition to the separation plane 586. While in other embodiments, the separation plane 586 may be shifted parallelly towards the first tooth 502 (i.e., in a direction of a normal vector to the separation plane 586 towards the first tooth 502) by the first separation distance 589. This shifted separation plane 586 may be referred to as the first cutting plane 588. Also, the separation plane 586 may be shifted parallelly towards the second tooth 504 (i.e., in a direction of a normal vector to the separation plane 586 towards the second tooth 504) by the second separation distance 590. This shifted separation plane 586 may be referred to as the second cutting plane 592.

In various non-limiting embodiments, the first separation distance 589 and the second separation distance 590 may be set by the orthodontic practitioner using the interactive user interface. In other embodiments, the processor 202 may be configured to set the first separation distance 589 and the second separation distance 590 based on the 3D digital model (e.g., the 3D digital model 500, 540, 560, and/or 580). It is to be noted that how the first separation distance 589 and the second separation distance 590 are set should not limit the scope of the present technology.

In certain embodiments, the first separation distance 589 may be equal to the second separation distance 590. While in other non-limiting embodiments, the first separation distance 589 may be different from the second separation distance 590. By way of an example, the first separation distance 589 may be more than the second separation distance 590. In another example, the first separation distance 589 may be less than the second separation distance 590 without limiting the scope of the technology.

For the purpose of understanding the first cutting plane 588 may be referred to as positive cutting plane 588 and the second cutting plane 592 may be referred to as negative cutting plane 592. The positive cutting plane 588 may intersect with the positive tooth 502, and the negative cutting plane 592 may intersect with the negative tooth 504.

STEP 408: Updating the 3D Digital Model by Removing Elements of the Two Adjacent Teeth which are Between the First and Second Cutting Planes The method 400 proceeds to step 408, where the processor 202 updates the 3D digital model (e.g., the 3D digital model 500, 540, 560, and/or 580) by removing first tooth elements 506, 546, and the second tooth elements 508, 548 which are located between the first cutting plane 588 and the second cutting plane 592.

Figure 12:
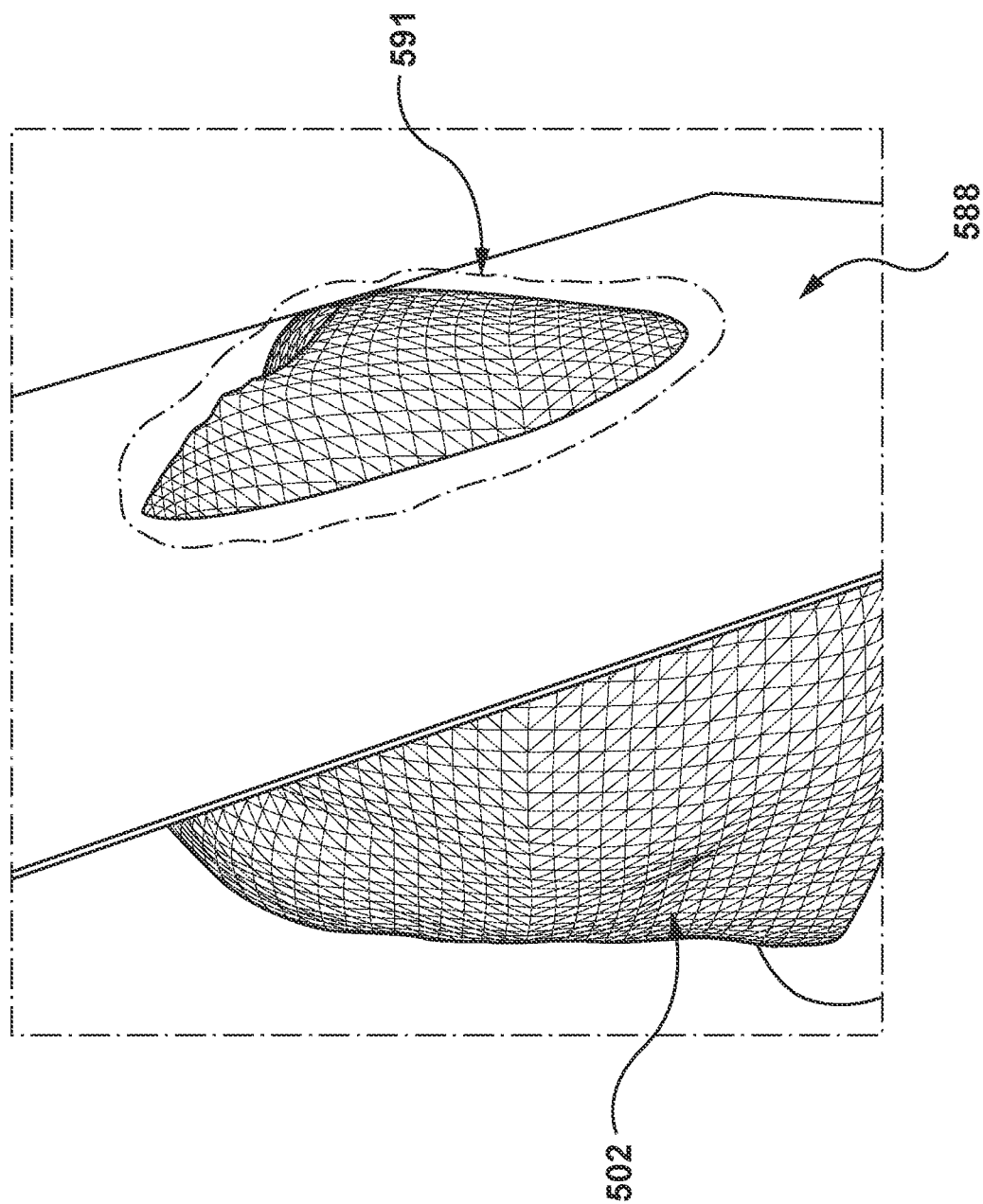
FIG. 12 illustrates an intersection of a positive plane with a positive tooth, in accordance with various non-limiting embodiments of the present technology.

FIG. 12 illustrates an intersection of the positive cutting plane 588 with the positive tooth 502, in accordance with various non-limiting embodiments of the present technology. As shown, the positive cutting plane 588 intersects with the positive tooth 502. While most of the elements associated the outer geometry of the positive tooth 502 lie on one side of the positive cutting plane 588, at least some of the elements 591 may lie on opposite side of the positive cutting plane 588. In other words, the at least some of the elements 591 may lie on an opposite side of the positive cutting plane 588 towards the negative tooth 504.

Figure 13:
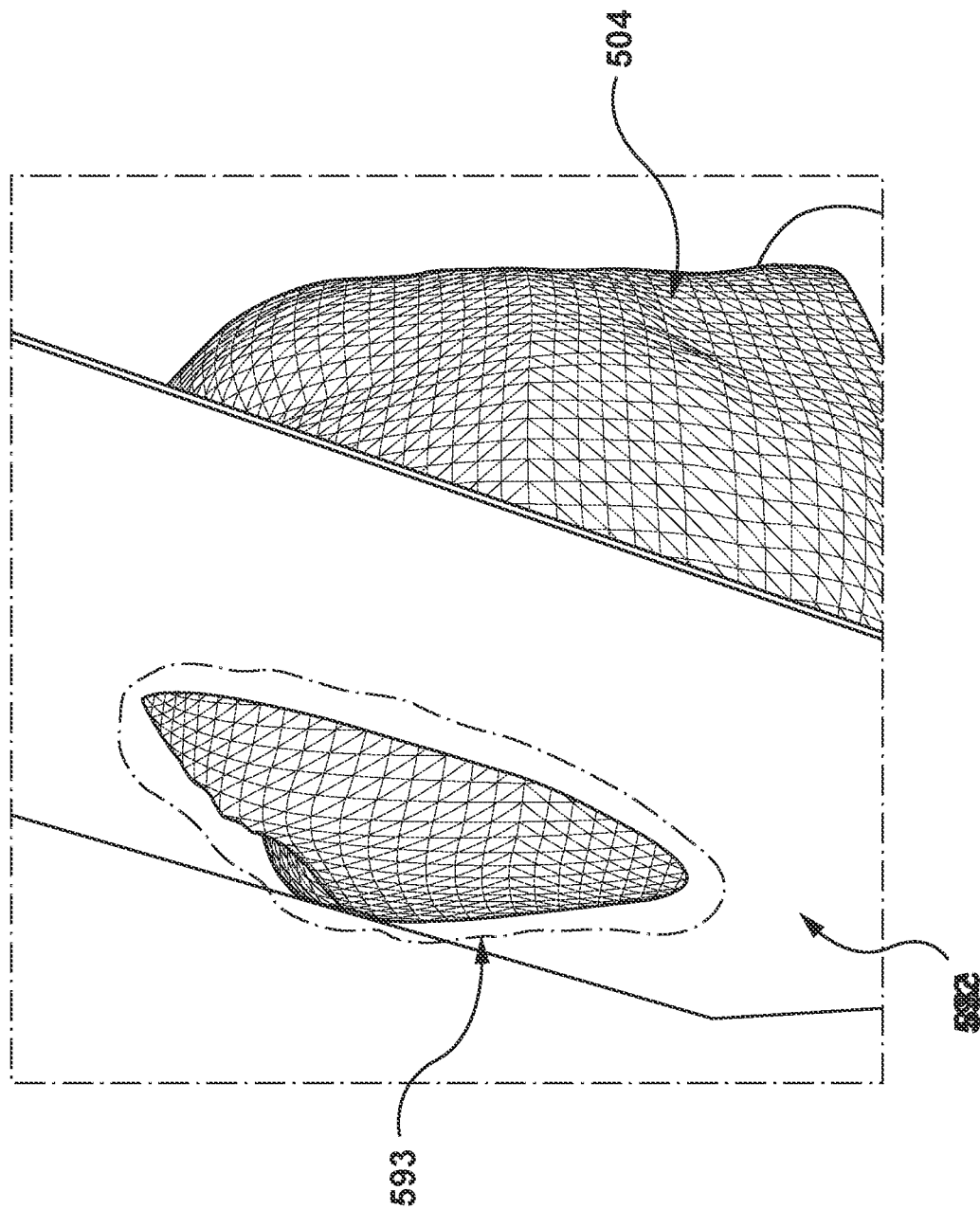
FIG. 13 illustrates an intersection of a negative plane with a negative tooth, in accordance with various non-limiting embodiments of the present technology.

Similarly, FIG. 13 illustrates an intersection of the negative cutting plane 592 with the negative tooth 504, in accordance with various non-limiting embodiments of the present technology. As shown, the negative cutting plane 592 intersects with the negative tooth 504. While most of the elements associated the outer geometry of the negative tooth 504 lie on one side of the negative cutting plane 592, at least some of the elements 593 may lie on an opposite side of the negative cutting plane 592. In other words, the at least some of the elements 593 may lie on opposite side of the negative cutting plane 592 towards the positive tooth 502.

In various non-limiting embodiments, the processor 202 may be configured to remove the at least some of the elements 591 and 593. In various non-limiting embodiments, the processor 202 may be configured to identify the at least some of the elements 591 to be removed by applying the following conditions:

$$\{(a_p x_i + b_p y_i + c_p z_i + d) < \text{first separation distance}\} \text{ for Positive tooth} \quad (15)$$

Where, $a_p$, $b_p$, $c_p$, and d are constant values associated with the positive cutting plane 588 and $x_i$, $y_i$, and $z_i$ are ith 3D Cartesian coordinates associated with the positive cutting plane 588.

In various non-limiting embodiments, the processor 202 may be configured to identify the at least some of the elements 593 to be removed by applying the following conditions:

$$\{(a_n x_i + b_n y_i + c_n z_i + d) > \text{second separation distance}\} \text{ for negative tooth} \quad (16)$$

Where, $a_n$, $b_n$, $c_n$, and d are constant values associated with the negative cutting plane 592 and $x_i$, $y_i$, and $z_i$ are ith 3D Cartesian coordinates associated with the negative cutting plane 592.

In accordance with various non-limiting embodiments, the processor 202 may be configured to project the at least some of the elements 591 and 593 on the positive cutting plane 588 and the negative cutting plane 592 respectively.

Figure 14:
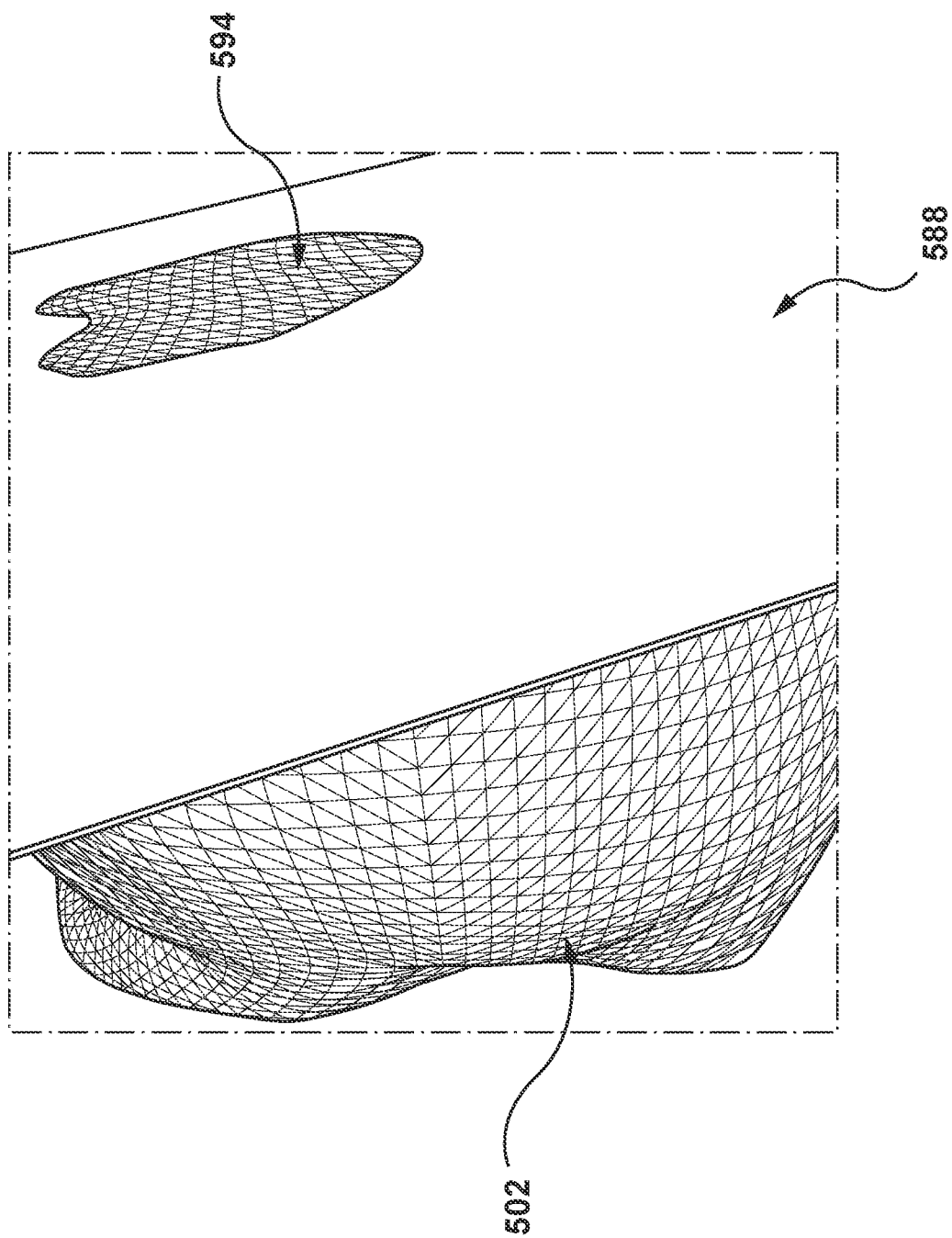
FIG. 14 illustrates projected elements on the positive plane, in accordance with various non-limiting embodiments of the present technology.
Figure 15:
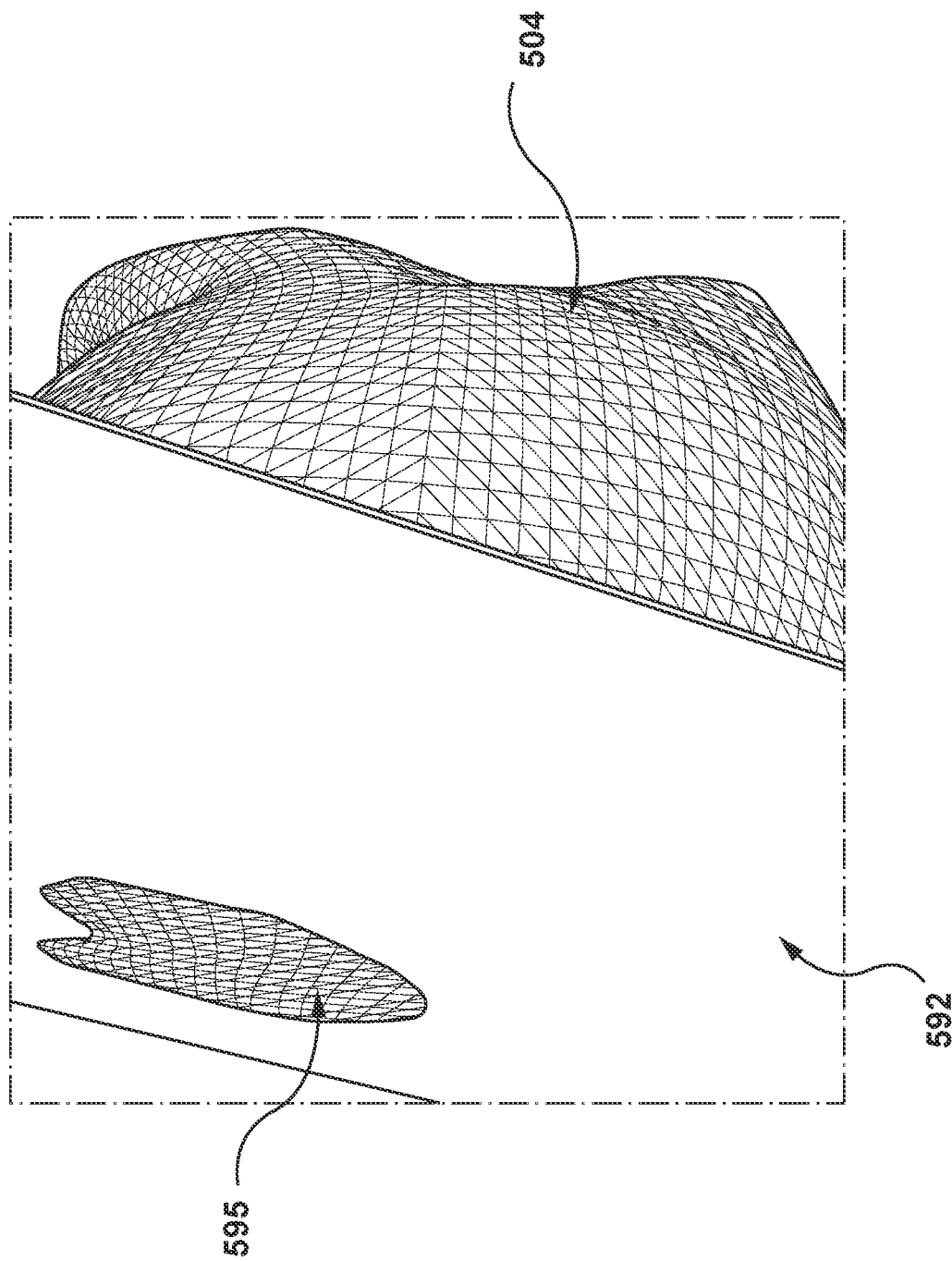
FIG. 15 illustrates projected elements on the negative plane, in accordance with various non-limiting embodiments of the present technology.

FIG. 14 illustrates projected elements 594 on the positive cutting plane 588, in accordance with various non-limiting embodiments of the present technology. FIG. 15 illustrates projected elements 595 on the negative cutting plane 592, in accordance with various non-limiting embodiments of the present technology.

In various non-limiting embodiments, the processor 202 may be configured to update the 3D digital model (e.g., the 3D digital model 500, 540, 560, and/or 580) by removing the projected elements 594 and 595.

The processor 202 may be configured to determine location of the updated elements associated with the positive tooth 502 from the following equations:

$$x_i' = x_i - a_p^*(a_p x_i + b_p y_i + c_p z_i + d) \quad (17)$$

$$y_i' = y_i - b_p^*(a_p x_i + b_p y_i + c_p z_i + d) \quad (18)$$

$$z_i' = z_i - c_p^*(a_p x_i + b_p y_i + c_p z_i + d) \quad (19)$$

Where, $a_p$, $b_p$, $c_p$ and d are constant values associated with the positive cutting plane 588, $x_i$, $y_i$, and $z_i$ are ith 3D Cartesian coordinates associated with the positive cutting plane 588, and $x'_i$, $y'_i$, and $z'_i$ are ith 3D Cartesian coordinates associated with updated locations of elements on the positive tooth 502.

In a similar manner, the processor 202 may be configured to determine location of the updated elements associated with the negative tooth 504 from the following equations:

$$x_i' = x_i - a_n(a_n x_i + b_n y_i + c_n z_i + d) \quad (20)$$

$$y_i' = y_i - b_n^*(a_n x_i + b_n y_i + c_n z_i + \quad (21)$$

$$z_i' = z_i - c_n^*(a_n x_i + b_n y_i + c_n z_i + d) \quad (22)$$

Where, $a_n$, $b_n$, $c_n$, and d, are constant values associated with the negative cutting plane 592, $x_i$, $y_i$, and $z_i$ are ith 3D Cartesian coordinates associated with the negative cutting plane 592, and $x'_i$, $y'_i$, and $z'_i$ are ith 3D Cartesian coordinates associated with updated locations of elements on the negative tooth 504.

Figure 16:
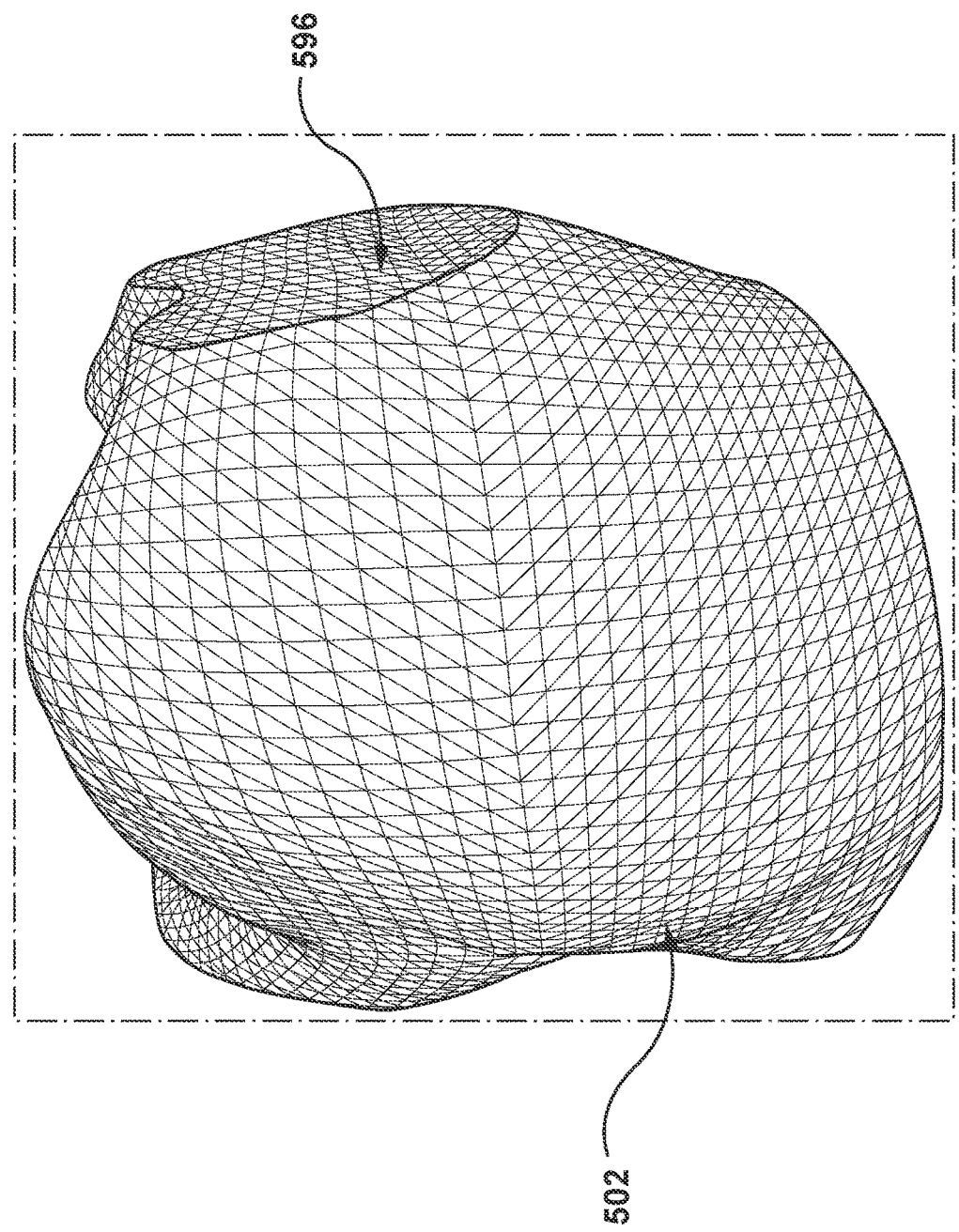
FIG. 16 illustrates the updated positive tooth, in accordance with various non-limiting embodiments of the present technology.
Figure 17:
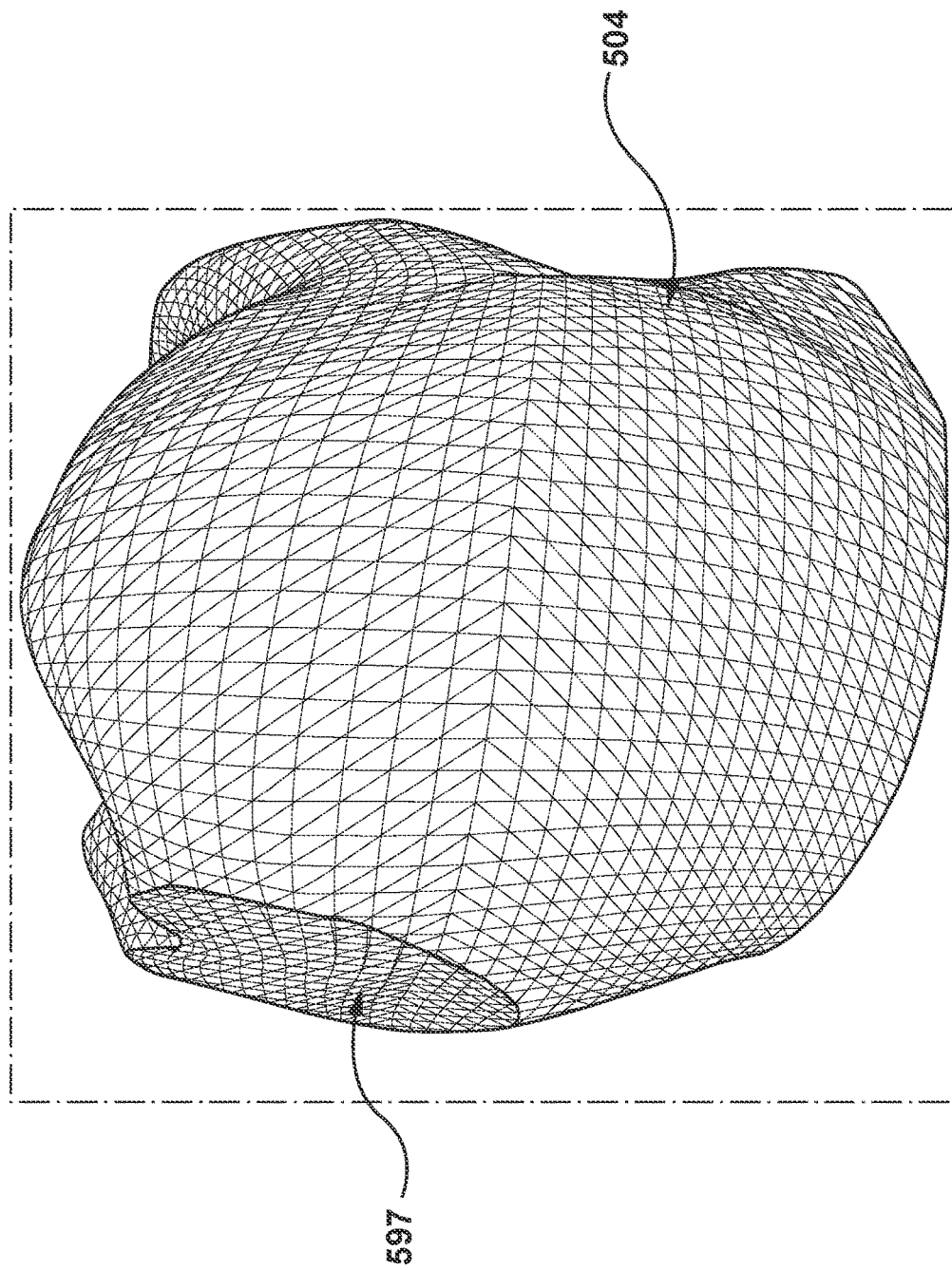
FIG. 17 illustrates the updated negative tooth, in accordance with various non-limiting embodiments of the present technology.

FIG. 16 illustrates a 3D digital model of the updated positive tooth 502, in accordance with various non-limiting embodiments of the present technology. FIG. 17 illustrates a 3D digital model of the updated negative tooth 504, in accordance with various non-limiting embodiments of the present technology.

Figure 18:
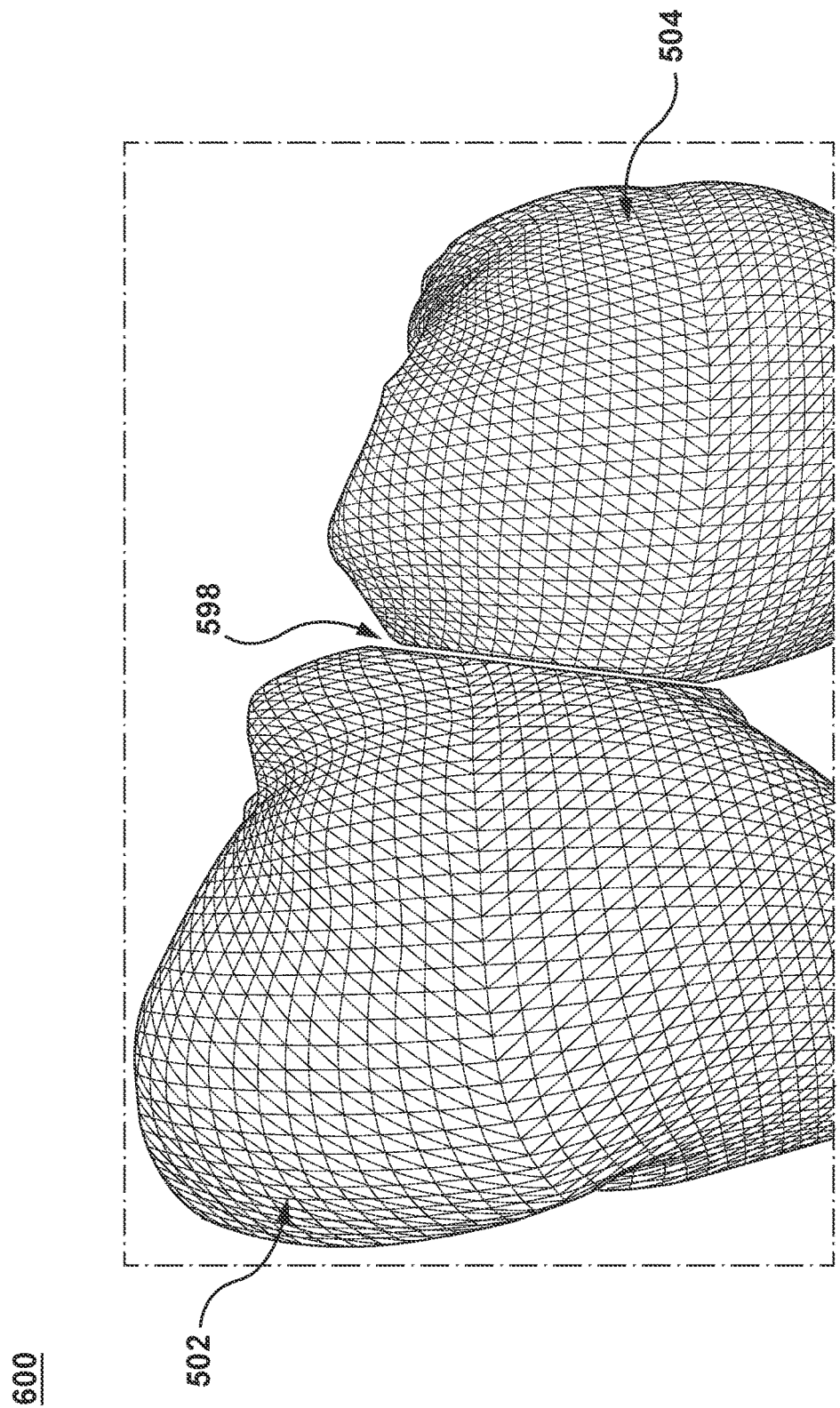
FIG. 18 illustrates the updated 3D digital model representing the updated positive tooth and updated negative tooth separated by an overall separation distance, in accordance with various non-limiting embodiments of the present technology.

FIG. 18 illustrates the updated 3D digital model 600 representing the updated positive tooth 502 and updated negative tooth 504 separated by an overall separation distance 598, in accordance with various non-limiting embodiments of the present technology.

In accordance with various non-limiting embodiments, the processor 202 may be configured to store the updated 3D digital model 600 in the one or more computer-readable storage media 208 associated with the computer system 110.

In accordance with various non-limiting embodiments, the processor 202 may be configured to display the updated 3D digital model 600 on the display screen 222 associated with the computer system 110.

In accordance with various non-limiting embodiments, the processor 202 may be configured to generate an orthodontic treatment plan for the patient in accordance with the updated 3D digital model 600.

In accordance with various non-limiting embodiments, the processor 202 may be configured to display the orthodontic treatment plan on the display screen 222 associated with the computer system 110. Based on the displayed orthodontic treatment plan, the orthodontic practitioner may perform an actual teeth separation on the patient. In various scenarios, where some modifications to the updated 3D digital model 600 may be required, the orthodontic practitioner may change various parameters on the interactive user interface. In return, the processor 202 may generate the updated 3D digital model 600 in accordance with the updated parameters. Such parameters may include but are not limited to predetermined distance, the first separation distance 589, the second separation distance 590, overall separation distance 598 or the like.

It is to be understood that the operations and functionality of computer system 110, constituent components, and associated processes may be achieved by any one or more of hardware-based, software-based, and firmware-based elements. Such operational alternatives do not, in any way, limit the scope of the present disclosure.

While the above-described implementations have been described and shown with reference to particular steps performed in a particular order, it will be understood that these steps may be combined, sub-divided, or re-ordered without departing from the teachings of the present technology. At least some of the steps may be executed in parallel or in series. Accordingly, the order and grouping of the steps is not a limitation of the present technology.

It should be expressly understood that not all technical effects mentioned herein need to be enjoyed in each and every embodiment of the present technology.

It will also be understood that, although the embodiments presented herein have been described with reference to specific features and structures, it is clear that various modifications and combinations may be made without departing from such disclosures. The specification and drawings are, accordingly, to be regarded simply as an illustration of the discussed implementations or embodiments and their principles as defined by the appended claims, and are contemplated to cover any and all modifications, variations, combinations or equivalents that fall within the scope of the present disclosure.

What is claimed is:

1. A method for performing digital separation of two adjacent teeth of a plurality of teeth of a patient, the method executable by a processor of a computer system, the method comprising:
   obtaining a 3D digital model of the two adjacent teeth, the two adjacent teeth comprising a first tooth and a second tooth, wherein the 3D digital model includes a first set of elements comprising first tooth elements representing a first outer geometry of the first tooth and second tooth elements representing a second outer geometry of the second tooth;
   generating a separation plane relative to the first tooth and the second tooth by:
      obtaining a second set of elements associated with a separation zone of the two adjacent teeth, the second set of elements comprising a first subset of the first set of elements;
      identifying a third set of elements which are a second subset of the second set of elements, such that the third set of elements includes a first portion of the first tooth elements in the separation zone being within a threshold distance from a second portion of the second tooth elements in the separation zone, and
      determining the separation plane based on the identified third set of elements, wherein:
         the threshold distance is a summation of a shortest distance between any two elements of the first tooth elements and the second tooth elements and a predetermined distance, and
         if the first outer geometry of the first tooth and the second outer geometry of the second tooth do not overlap with each other, the identifying the third set of elements comprises:
            identifying a closest element pair comprising a first element associated with the first tooth elements and a second element associated with the second tooth elements that are separated by the shortest distance, and
            determining the third set of elements comprises identifying element pairs, each element pair comprising the first element associated with the first tooth elements and the second element associated with the second tooth elements that are within the summation of the shortest distance and the predetermined distance;
   performing the digital separation by generating a first cutting plane and a second cutting plane, the first cutting plane being parallel to the separation plane and spaced therefrom towards the first tooth by a first separation distance, and the second cutting plane being parallel to the separation plane and spaced therefrom towards the second tooth by a second separation distance;
   updating the 3D digital model by removing the first tooth elements and the second tooth elements which are between the first cutting plane and the second cutting plane, the updated 3D digital model representing the digitally separated two adjacent teeth; and
   storing the updated 3D digital model in a memory of the computer system.

2. The method of claim 1, wherein,
   the threshold distance is a predetermined distance, and
   if the first outer geometry of the first tooth and the second outer geometry of the second tooth overlap with each other, the identifying the third set of elements comprises identifying element pairs, each element pair comprising a first element associated with the first tooth elements and a second element associated with the second tooth elements that are within the predetermined distance.

3. The method of claim 1, further comprising computing the shortest distance by one or more of:
using a bounding volume hierarchy (BVH) structure;
converting at least one of the first outer geometry and the second outer geometry into a distance field data structure;
reducing a dimensionality of the first set of elements in the 3D digital model of the two adjacent teeth from 3D Cartesian coordinates to 2D UV Cartesian coordinates.

4. The method of claim 3, wherein the distance field data structure includes precomputed shortest distances from the first tooth elements to the second tooth elements.

5. The method of claim 3, wherein the reducing the dimensionality of the first set of elements in the 3D digital model of the two adjacent teeth includes:
defining a uniform 2D grid representing the 3D digital model, the 2D grid including a plurality of 2D grid cells such that a given 2D grid cell of the plurality of 2D grid cells corresponds to a respective one of the first tooth elements and the second tooth elements of the first set of elements in the 3D digital model; and
assigning, to each one of the plurality of 2D grid cells, a first depth value and a second depth value, the second depth value being greater than the first depth value.

6. The method of claim 5, wherein the method further comprises computing the shortest distance between the first element associated with the first tooth elements and the second element associated with the second tooth elements based on the first depth value, the second depth value.

7. The method of claim 1, wherein the determining the separation plane according to the identified third set of elements includes a planar fitting of coordinates of the identified third set of elements based on linear regression and the threshold distance.

8. The method of claim 1, wherein the first separation distance is equal to the second separation distance.

9. The method of claim 1, wherein the first separation distance is different from the second separation distance.

10. The method of claim 1, wherein the 3D digital model is based on at least one of:
axis-aligned bounding boxes (AABB) and the first set of elements representing the first outer geometry and the second outer geometry comprise a set of AABA vertices;
a 3D point cloud and the first set of elements representing the first outer geometry and the second outer geometry comprise points;
a polygon mesh and the first set of elements representing the first outer geometry and the second outer geometry comprise a set of mesh vertices.

11. The method of claim 1, further comprising, generating an orthodontic treatment plan for the patient in accordance with the updated 3D digital model.

12. The method of claim 11, further comprising, displaying the orthodontic treatment plan.

13. The method of claim 1, further comprising, displaying the updated 3D digital model.

14. The method of claim 1, wherein,
at least some of the first tooth elements and the second tooth elements of the second set of elements associated with the first tooth are projected on the first cutting plane,
at least some of the first tooth elements and the second tooth elements of the second set of elements associated with the second tooth are projected on the second cutting plane, and
the updating the 3D digital model, further comprises, removing the elements of the second set of elements projected on the first cutting plane and the second cutting plane.

15. The method of claim 1, wherein the separation zone includes an interdental region between the first tooth and the second tooth.

16. A system for performing digital separation of two adjacent teeth of a plurality of teeth of a patient, the system comprising a computer system having a processor, the processor configured to execute a method comprising:
obtaining a 3D digital model of the two adjacent teeth, the two adjacent teeth comprising a first tooth and a second tooth, wherein the 3D digital model includes a first set of elements comprising first tooth elements representing a first outer geometry of the first tooth and second tooth elements representing a second outer geometry of the second tooth;
generating a separation plane relative to the first tooth and the second tooth by:
obtaining a second set of elements associated with a separation zone of the two adjacent teeth, the second set of elements comprising a first subset of the first set of elements;
identifying a third set of elements which are a second subset of the second set of elements, such that the third set of elements includes a first portion of the first tooth elements in the separation zone being within a threshold distance from a second portion of the second tooth elements in the separation zone, and
determining the separation plane based on the identified third set of elements, wherein:
the threshold distance is a summation of a shortest distance between any two elements of the first tooth elements and the second tooth elements and a predetermined distance, and
if the first outer geometry of the first tooth and the second outer geometry of the second tooth do not overlap with each other, the identifying the third set of elements comprises:
identifying a closest element pair comprising a first element associated with the first tooth elements and a second element associated with the second tooth elements that are separated by the shortest distance, and
determining the third set of elements comprises identifying element pairs, each element pair comprising the first element associated with the first tooth elements and the second element associated with the second tooth elements that are within the summation of the shortest distance and the predetermined distance;
performing the digital separation by generating a first cutting plane and a second cutting plane, the first cutting plane being parallel to the separation plane and spaced therefrom towards the first tooth by a first separation distance, and the second cutting plane being parallel to the separation plane and spaced therefrom towards the second tooth by a second separation distance;
updating the 3D digital model by removing the first tooth elements and the second tooth elements which are between the first cutting plane and second cutting plane, the updated 3D digital model representing the digitally separated two adjacent teeth; and storing the updated 3D digital model in a memory of the computer system.

17. The system of claim 16, wherein, the threshold distance is a predetermined distance, and if the first outer geometry of the first tooth and the second outer geometry of the second tooth overlap with each other, the identifying the third set of elements comprises identifying element pairs, each element pair comprising a first element associated with the first tooth elements and a second element associated with the second tooth elements that are within the predetermined distance.

18. The system of claim 16, wherein the determining the separation plane according to the identified third set of elements includes a planar fitting of coordinates of the identified third set of elements based on linear regression and the threshold distance.

* * * * *